(12) United States Patent
Biebl et al.

(10) Patent No.: US 11,958,890 B2
(45) Date of Patent: *Apr. 16, 2024

(54) ANTIMICROBIAL PROTEINS

(71) Applicant: LYSANDO AG, Triesenberg (LI)

(72) Inventors: Manfred Biebl, Obertraubling (DE); Martin Griessl, Hemau (DE)

(73) Assignee: LYSANDO AG, Triesenberg (LI)

( * ) Notice: Subject to any disclaimer, the term of this patent is extended or adjusted under 35 U.S.C. 154(b) by 7 days.

This patent is subject to a terminal disclaimer.

(21) Appl. No.: 17/057,933

(22) PCT Filed: May 29, 2019

(86) PCT No.: PCT/EP2019/064100
§ 371 (c)(1),
(2) Date: Nov. 23, 2020

(87) PCT Pub. No.: WO2019/229185
PCT Pub. Date: Dec. 5, 2019

(65) Prior Publication Data
US 2021/0300979 A1    Sep. 30, 2021

(30) Foreign Application Priority Data
May 30, 2018    (EP) .................... 18175155

(51) Int. Cl.
| | | |
|---|---|---|
| *C07K 14/47* | (2006.01) | |
| *A01N 63/50* | (2020.01) | |
| *A61K 38/00* | (2006.01) | |
| *A61P 31/04* | (2006.01) | |
| *C07K 14/435* | (2006.01) | |
| *C12N 9/36* | (2006.01) | |

(52) U.S. Cl.
CPC .......... *C07K 14/4723* (2013.01); *A01N 63/50* (2020.01); *A61P 31/04* (2018.01); *C07K 14/43563* (2013.01); *C12N 9/2462* (2013.01); *C12Y 302/01017* (2013.01); *A61K 38/00* (2013.01); *C07K 2319/00* (2013.01)

(58) Field of Classification Search
CPC .......... C07K 14/4723; C07K 14/43563; C07K 2319/00; A61P 31/04; A01N 63/50; C12N 9/2462; C12Y 302/01017; A61K 38/00
See application file for complete search history.

(56) References Cited

U.S. PATENT DOCUMENTS

| | | |
|---|---|---|
| 8,906,365 B2 | 12/2014 | Lavigne et al. |
| 9,737,579 B2 | 8/2017 | Da Costa Garcia et al. |
| 2007/0207209 A1 | 9/2007 | Murphy et al. |
| 2011/0243915 A1 | 10/2011 | Briers et al. |
| 2012/0189606 A1* | 7/2012 | Lavigne ............... A61P 31/00 435/7.1 |

FOREIGN PATENT DOCUMENTS

| | | |
|---|---|---|
| CN | 105 237 630 | 1/2016 |
| EP | 2468856 A1 | 6/2012 |
| EP | 3129044 B1 | 9/2022 |
| JP | 2012-500642 | 3/2010 |
| JP | 2012-530509 A | 12/2012 |
| JP | 2013-81465 | 5/2013 |
| JP | 2013-532955 | 8/2013 |
| JP | 2021-525072 A | 9/2021 |
| JP | 2021-525092 A | 9/2021 |
| WO | WO 2010/023207 | 3/2010 |
| WO | WO 2010/141135 A2 | 12/2010 |
| WO | WO 2010/149792 | 12/2010 |
| WO | WO 2010/149795 | 12/2010 |
| WO | WO 2011/023702 | 3/2011 |
| WO | WO 2011/134998 | 11/2011 |

(Continued)

OTHER PUBLICATIONS lysozyme murein hydrolase [Enterobacter phage CC31], from https://www.ncbi.nlm.nih.gov/protein/ADB81628.1?report=genbank&log$=protalign&blast_rank=1&RID=N0D4U95401N, Nov. 10, 2010, pp. 1-2.*
lysozyme murein hydrolase [Serratia phage CHI14], from https://www.ncbi.nlm.nih.gov/protein/ARW57549.1?report=genbank&log$=protalign&blast_rank=1&RID=N0FD29N5013, Jun. 11, 2017, pp. 1-2.*
Gong et al, How do antimicrobial peptides disrupt the lipopolysaccharide membrane leaflet of Gram-negative bacteria?, Journal of Colloid and Interface Science, 2023, 637, pp. 182-192.*
International Search Report and Written Opinion issued in International Application No. PCT/EP2019/064100, dated Jul. 24, 2019.
Briers et al., "A standardized approach for accurate quantification of murein hydrolase activity in high-throughput assays." *Journal of biochemical and biophysical methods* 70.3 (2007): 531-533.
Database UniParc, UPI003C150BE, 2013.

(Continued)

*Primary Examiner* — Li N Komatsu
(74) *Attorney, Agent, or Firm* — Parker Highlander PLLC

(57) ABSTRACT

The present invention relates to a polypeptide comprising a Gram negative endolysin and a peptide selected from the group consisting of an antimicrobial peptide, an amphipathic peptide, a cationic peptide, a sushi peptide or a defensin, wherein the endolysin in turn is selected from the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9 and sequences having at least 80% sequence identity with SEQ ID NO:1, SEQ ID NO:2, SEQ ID NO:3, SEQ ID NO:4, SEQ ID NO:5, SEQ ID NO:6, SEQ ID NO:7, SEQ ID NO:8 and/or SEQ ID NO:9. The present invention relates also to corresponding nucleic acids, vectors, bacteriophages, host cells, compositions and kits. The present inventions also relates to the use of said polypeptides, nucleic acids, vectors, bacteriophages, host cells, compositions and kits in methods for treatment of the human or animal body by surgery or therapy or in diagnostic methods practiced on the human or animal body. The polypeptides, nucleic acids, vectors, bacteriophages, host cells, compositions and kits according to the invention may also be used as an antimicrobial in, e.g., food or feed, in cosmetics, or as disinfecting agent.

14 Claims, 1 Drawing Sheet
Specification includes a Sequence Listing.

(56) References Cited

FOREIGN PATENT DOCUMENTS

| WO | WO 2012/036580 | 3/2012 |
|----|----|----|
| WO | WO 2012/059545 | 5/2012 |
| WO | WO 2012/146738 | 11/2012 |
| WO | WO 2015/005787 A1 | 1/2015 |
| WO | WO 2015/121443 | 8/2015 |
| WO | WO 2015/155244 | 10/2015 |
| WO | WO 2015/155244 A1 | 10/2015 |
| WO | WO 2017/186942 | 11/2017 |
| WO | WO 2018/073416 | 4/2018 |
| WO | WO 2018/091707 | 5/2018 |
| WO | WO 2018/109229 | 6/2018 |
| WO | WO 2019/229184 A1 | 12/2019 |
| WO | WO 2019/229185 A1 | 12/2019 |

OTHER PUBLICATIONS

Ding et al., "The Sushi peptides: structural characterization and mode of action against Gram-negative bacteria." *Cellular and Molecular Life Sciences* 65.7 (2008): 1202-1219.

Donovan et al., "Lysis of staphylococcal mastitis pathogens by bacteriophage phi11 endolysin." *FEMS microbiology letters* 265.1 (2006): 133-139.

EBI, GSP:BDB58489; 2016.

Hugo et al., "Characterization and genome sequencing of a Citrobacter freundii phage. CfP1 harboring a lysin active against multidrug-resistant isolates." *Applied microbiology and biotechnology* 100.24 (2016): 10543-10553.

International Search Report and Written Opinion issued in International Application No. PCT/EP2019/064097, dated Nov. 6, 2019.

Memo regarding Nucleic Acid and Peptide Claim interpretations; dated Dec. 29, 2005.

Office Communication issued in correspondence Eurasian Application No. 2019/91233 dated Oct. 27, 2021 {English Translation}.

Office Communication issued in correspondence Japanese Application No. 2019/532685 dated Oct. 13, 2021 {English Translation}.

Office Communication issued in correspondence U.S. Appl. No. 16/469,800 dated Aug. 4, 2021.

Office Communication issued in correspondence U.S. Appl. No. 16/469,800 dated Dec. 16, 2021.

Pirnay et al., "Analysis of the Pseudomonas aeruginosa oprD gene from clinical and environmental isolates." *Environmental microbiology* 4.12 (2002): 872-882.

Schmelcher et al., "Bacteriophage endolysins as novel antimicrobials." *Future microbiology* 7.10 (2012): 1147-1171.

Skerlavaj et al., "SMAP-29: a potent antibacterial and antifungal peptide from sheep leukocytes", FEBS, vol. 463, No. 1-2, p. 58-62, 1999.

Tan et al., "High-affinity LPS binding domain (s) in recombinant factor C of a horseshoe crab neutralizes LPS-induced lethality." *The FASEB Journal* 14.7 (2000): 859-870.

Vaara, "Agents that increase the permeability of the outer membrane"; Microbiological Reviews, 1992, p. 395-411.

Walmagh et al., "Development and evaluation of engineered bacteriophage endolysins to inactivate Gram-negative bacteria." Dissertation, KU Leuven (2013).

Zhang et al. "Multiple-site mutations of phage Bp7 endolysin improves its activities against target bacteria." *Virologica Sinica* 30.5 (2015): 386-395.

Borysowski, J. et al., "Bacteriophage Endolysins as a Novel Class of Antibacterial Agents," *Society for Experimental Biology and Medicine*, (2005): 366-377.

Briers, Y. et al., "Art-175 Is a Highly Efficient Antibacterial against Multidrug-Resistant Strains and Persisters of *Pseudomonas aeruginosa*," *Antimicrobial Agents and Chemotherapy*, 58 (2014): 3774-3784.

Briers, Y. et al., "Engineered Endolysin-Based "Artilysins" To Combat Multidrug-Resistant Gram-Negative Pathogens," *mBio*, 5 (2014): 1-32.

Briers, Y. et al., "The high-affinity peptidoglycan binding domain of *Pseudomonas* phage endolysin KZ144," *Biochemical and Biophysical Research Communications*, 383 (2009): 187-191.

Briers, Y. et al., "Use of bacteriophage endolysin EL188 and outer membrane permeabilizers against *Pseudomonas aeruginosa*," *Journal of Applied Microbiology*, 100 (2011): 778-785.

Certified Priority Document of EP Application No. 14163927.8, filed Apr. 8, 2014, 121 pages.

Fischetti, V., "Bacteriophage endolysins: A novel anti-effective to control Gram-positive pathogens," *International Journal of Medical Microbiology*, 300 (2010): 357-362.

Fischetti, V., "Bacteriophage Lysins as Effective Antibacterials," *Curr Opin Microbiology*, 11 (2008): 393-400.

Gutiérrez, D. et al., "Effective Removal of Staphylococcal Biofilms by the Endolysin LysH5," *PLOAS ONE*, 9 (2014): 1-8.

Hurley, M. N. et al., "Novel approaches to the treatment of *Pseudomonas aeruginosa* infections in cystic fibrosis," *Eur Respir J.*, 40 (2012): 1014-1023.

Nelson, D. C. et al., "Endolysins as Antimicrobials," *Advances in Virus Research*, 83 (2012): 299-365.

PCT International Search Report and Written Opinion issued in International Patent Application No. PCT/EP2015/057625, dated Oct. 12, 2016.

Quickel, Jr., K. E. et al., "Efficacy and Safety of Topical Lysostaphin Treatment of Persistent Nasal Carriage of *Staphylococcus aureus*," *Applied Microbiology*, 22 (1971): 446-450.

Schmelcher, M. et al., "Bacteriophage endolysins as novel antimicrobials," *Future Microbiology*, 7 (2012): 1147-1171.

Submission in European Patent Application No. 15715243.0, dated Oct. 16, 2018, 7 pages.

Teneback, C. C. et al., "Bioengineered Lysozyme Reduces Bacterial Burden and Inflammation in a Murine Model of Mucoid *Pseudomonas aeruginosa* Lung Infection," *Antimicrobial Agents and Chemotherapy*, 57 (2013): 5559-5564.

Vesga, O. et al., "*Staphylococcus aureus* Small Colony Variants Are Induced by the Endothelial Cell Intracellular Milieu," *The Journal of Infectious Diseases*, 173 (1996): 739-742.

Walmagh, M. et al., "Characterization of Modular Bacteriophage Endolysins from *Myoviridae* Phages OBP, 201φ2-1 and PVP-SE1," *PLOS ONE*, 7 (2012): 1-10.

Notification of Refusal issued in Japanese Patent Application No. 2020-564849, dated Apr. 25, 2023 (with English Translation).

Notification of Refusal issued in Japanese Patent Application No. 2020-565937, dated Apr. 25, 2023 (with English Translation).

\* cited by examiner

| Sequence motif alternative \ Position | 1 | 2 | 3 | 4 | 5 | 6 | 7 | 8 | 9 | 10 | 11 | 12 | 13 | 14 | 15 | 16 | 17 | 18 | 19 | 20 |
|---|---|---|---|---|---|---|---|---|---|---|---|---|---|---|---|---|---|---|---|---|
| 1 |  |  | x | x |  |  | x |  |  |  | x |  |  | x | x |  |  | x |  |  |
| 2 |  |  | x | x |  |  | x |  |  |  | x |  |  | x |  |  |  | x |  |  |
| 3 |  |  | x |  |  |  | x |  |  |  | x |  |  | x |  |  | x | x |  |  |
| 4 |  |  | x |  |  |  | x |  |  | x |  |  |  | x |  |  | x | x |  |  |
| 5 |  | x | x |  |  | x | x |  |  | x |  |  |  | x |  |  | x |  |  | x |
| 6 |  | x | x |  |  | x |  |  |  | x |  |  | x | x |  |  | x |  |  | x |
| 7 |  | x |  |  |  | x |  |  |  | x |  |  | x |  |  |  | x |  |  | x |
| 8 |  | x |  |  | x | x |  | x | x | x |  |  | x |  |  |  | x |  |  | x |
| 9 | x | x |  |  | x | x |  | x | x | x |  |  | x |  |  | x | x |  |  | x |
| 10 | x |  |  |  | x | x |  | x | x |  |  | x | x |  |  | x | x |  |  | x |
| 11 | x |  |  |  | x |  |  | x | x |  |  | x | x |  |  | x |  |  | x | x |
| 12 | x |  |  |  | x |  |  |  | x |  |  | x |  |  |  | x |  |  | x | x |
| 13 | x |  |  |  | x |  |  |  |  |  | x | x | x |  | x | x |  |  | x |  |
| 14 | x |  |  | x |  |  |  | x |  |  | x | x |  |  | x | x |  |  | x |  |
| 15 | x |  |  | x |  |  |  | x |  |  | x | x |  |  | x |  |  |  | x |  |
| 16 |  |  |  | x |  |  | x |  |  |  |  |  |  |  | x |  |  | x | x |  |
| 17 |  |  |  | x |  |  | x |  |  |  |  |  |  | x | x |  |  | x | x |  |
| 18 |  |  |  | x |  |  |  |  |  |  |  |  |  |  | x |  |  | x |  |  |

ANTIMICROBIAL PROTEINS

This application is a national phase application under 35 U.S.C. § 371 of International Application No. PCT/EP2019/064100, filed May 29, 2019, which claims benefit of priority to European Application No. 18175155.3, filed May 30, 2018, the entire contents of each of which are hereby incorporated by reference.

The present invention relates to a polypeptide comprising a Gram negative endolysin and a peptide selected from the group consisting of an antimicrobial peptide, an amphipathic peptide, a cationic peptide, a sushi peptide or a defensin, wherein the endolysin in turn is selected from the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9 and sequences having at least 80% sequence identity with SEQ ID NO:1, SEQ ID NO:2, SEQ ID NO:3, SEQ ID NO:4, SEQ ID NO:5, SEQ ID NO:6, SEQ ID NO:7, SEQ ID NO:8 and/or SEQ ID NO:9. The present invention relates also to corresponding nucleic acids, vectors, bacteriophages, host cells, compositions and kits. The present inventions also relates to the use of said polypeptides, nucleic acids, vectors, bacteriophages, host cells, compositions and kits in methods for treatment of the human or animal body by surgery or therapy or in diagnostic methods practiced on the human or animal body. The polypeptides, nucleic acids, vectors, bacteriophages, host cells, compositions and kits according to the invention may also be used as an antimicrobial in, e.g., food or feed, in cosmetics, or as disinfecting agent.

Resistance to conventional antibiotics is becoming an increasing health risk for humankind New antibiotics resistance mechanisms are emerging and rapidly spreading globally. Consequently, the ability to treat common infectious diseases may become more and more difficult in the near future. This danger has been readily understood in the art and new approaches to combat bacterial infectious agents are explored.

Among these new approaches is the creation of fusion proteins combining endolysins with different kinds of peptides. Endolysins are muralytic enzymes (in particular peptidoglycan hydrolases) encoded by bacteriophages (i.e. bacterial viruses). They are synthesized during late gene expression in the lytic cycle of phage multiplication and mediate the release of progeny virions from infected cells through degradation of the bacterial peptidoglycan. In terms of enzymatic activity they are usually either ß(1,4)-glycosylases (lysozymes), transglycosylases, amidases or endopeptidases. Antimicrobial application of endolysins was already suggested in 1991. Although the killing capacity of endolysins has been known for a long time, the use of these enzymes as antibacterials was ignored due to the success and dominance of antibiotics. Only after the appearance of multiple antibiotic resistant bacteria this simple concept of combating human pathogens with endolysins received interest. A compelling need to develop totally new classes of antibacterial agents emerged and endolysins used as 'enzybiotics'—a hybrid term of 'enzymes' and 'antibiotics'—perfectly met this need. In 2001, Fischetti and coworkers demonstrated for the first time the therapeutic potential of bacteriophage Cl endolysin towards group A streptococci. Since then many publications have established endolysins as an attractive and complementary alternative to control bacterial infections, particularly by Gram positive bacteria. Subsequently different endolysins against other Gram positive pathogens such as *Streptococcus pneumoniae*, *Bacillus anthracis*, *S. agalactiae* and *Staphylococcus aureus* have proven their efficacy as enzybiotics. For a long time then, the most important challenge of endolysin therapy laid in the insensitivity of Gram-negative bacteria towards the exogenous action of endolysins, since the outer membrane shields the access of endolysins from the peptidoglycan.

Gram-negative bacteria possess an outer membrane, with its characteristic asymmetric bilayer as a hallmark. The outer membrane bilayer consists of an inner monolayer containing phospholipids (primarily phosphatidyl ethanolamine) and an outer monolayer that is mainly composed of a single glycolipid, lipopolysaccharide (LPS). There is an immense diversity of LPS structures in the bacterial kingdom and the LPS structure may be modified in response to prevailing environmental conditions. The stability of the LPS layer and interaction between different LPS molecules is mainly achieved by the electrostatic interaction of divalent ions (Mg2+, Ca2+) with the anionic components of the LPS molecule (phosphate groups in the lipid A and the inner core and carboxyl groups of KDO). Furthermore, the dense and ordered packing of the hydrophobic moiety of lipid A, favored by the absence of unsaturated fatty acids, forms a rigid structure with high viscosity. This makes it less permeable for lipophilic molecules and confers additional stability to the outer membrane (OM).

In order to overcome the shielding effect of the outer membrane, endolysins of Gram negative bacteria have been meanwhile successfully fused with, e.g. cationic, amphipathic, hydrophobic or antimicrobial peptides. Such fusion proteins are capable of eliminating Gram negative bacteria when added from without (see for example WO 2010/023207, WO 2010/149792, WO 2011/134998, WO 2012/146738, or WO 2015/121443). However, for achieving improved antibacterial activity, said fusion proteins are frequently combined with small amounts of ethylene diamine tetraacetic acid (EDTA). EDTA is a chelator and known outer membrane permeabilizer (Vaara, M. Microbiol. Rev. 1992 September; 56 (3):395-411, incorporated herein by reference). By removing divalent cations from their binding cites, a disruption of the outer membrane is caused, which typically improves the antibacterial activity of the above mentioned fusion proteins (see for example WO 2010/023207, tables 6 and 8).

While there are various fields of application where the use of EDTA is perfectly acceptable (e.g. in a disinfectant), there are other fields of use where the parallel use of EDTA or other outer membrane permeabilizers is suboptimal or even undesirable (e.g., in the fields of animal feed, food safety, medical devices, and in the pharmaceutical field in general), because EDTA will unspecifically form a complex with any kind of cations, not only those of the bacterial membrane.

Therefore, there is still a need in the art for further improvement in the design of such antibacterial fusion proteins, in particular for applications which do not allow parallel use of EDTA.

The problem to be solved by the present invention was thus to provide new antimicrobial agents of the aforementioned type, which exhibit (in particular under physiological conditions) antibacterial activity and are less dependent on the parallel presence of EDTA or other outer membrane permeabilizing substances.

This problem is solved by the subject-matter as set forth in the appended claims and in the description below.

The inventors of the present invention have surprisingly found that a specific type of endolysins is particularly useful when fused to cationic, amphipathic or antimicrobial peptides. The resulting fusion proteins exhibit a significant antibacterial activity if added from without to Gram negative bacteria such as *E. coli*, and are, surprisingly, at the same time much less dependent on the parallel presence of EDTA as permeabilizer of the outer membrane of Gram negative bacteria than other antibacterial fusion proteins of this kind. This surprising property renders these polypeptides particularly suited for application in EDTA sensitive fields of use.

The term "polypeptide" as used herein refers in particular to a polymer of amino acid residues linked by peptide bonds in a specific sequence. The amino acid residues of a polypeptide may be modified by e.g. covalent attachments of various groups such as carbohydrates and phosphate. Other substances may be more loosely associated with the polypeptide, such as heme or lipid, giving rise to conjugated polypeptides which are also comprised by the term "polypeptide" as used herein. The term as used herein is intended to encompass also proteins. Thus, the term "polypeptide" also encompasses for example complexes of two or more amino acid polymer chains. The term "polypeptide" does encompass embodiments of polypeptides which exhibit optionally modifications typically used in the art, e.g. biotinylation, acetylation, pegylation, chemical changes of the amino-, SH- or carboxyl-groups (e.g. protecting groups) etc. As will become apparent from the description below, the polypeptide according to the invention is an artificially engineered polypeptide, which does not exist in this form in nature. Such polypeptide may for example exhibit artificial mutations vis-à-vis a naturally occurring polypeptide or may comprise heterologous sequences, or may be a fragment of a naturally occurring polypeptide, which fragment does not occur in this form in nature. Furthermore, the polypeptide according to the present invention is a fusion protein, i.e. represents the linkage of at least two amino acid sequences which do not occur in this combination in nature. The term "polypeptide" as used herein is not limited to a specific length of the amino acid polymer chain. Usually, but not necessarily, a typical polypeptide of the present invention will not exceed about 1000 amino acids in length. The inventive polypeptide may for instance be at most about 750 amino acids long, at most about 500 amino acids long or at most about 300 amino acids long. A possible length range for the inventive polypeptide, without being limited thereto, may thus for example be 16 to 1000 amino acids, 16 to about 50 amino acids, about 200 to about 750 amino acids, or about 225 to about 600 amino acids, or about 250 to about 350 amino acids.

The term "muralytic enzyme", as used herein, is generally understood in the art. It refers to any polypeptide which is capable of hydrolyzing the peptidoglycan of bacteria, such as Gram negative bacteria. The term is not restricted to a specific enzymatic cleavage mechanism. In terms of cleavage mechanism, the muralytic enzyme may be for example an endopeptidase, chitinase, T4 like muraminidase, lambda like muraminidase, N-acetyl-muramoyl-L-alanine-amidase (amidase), muramoyl-L-alanine-amidase, muramidase, lytic transglycosylase (C), lytic transglycosylase (M), N-acetyl-muramidase (lysozyme), N-acetyl-glucosaminidase or transglycosylases. Furthermore, the term encompasses naturally occurring muralytic enzymes, such as muralytic enzymes (e.g. peptidoglycan hydrolases) of eukaryotic, prokaryotic or viral (in particular bacteriophage) origin. The term encompasses for example vertebrate lysozymes (such as hen egg white lysozyme and human lysozyme), endolysins (e.g. KZ144 endolysin or Lys394 endolysin), Virion-associated peptidoglycan hydrolases (VAPGH), bacteriocins (e.g. lysostaphin) and autolysins. The "muralytic enzyme" may also be a synthetic or artificially modified polypeptide capable of cleaving the peptidoglycan of bacteria. For example, enzymatically active shuffled endolysins in which domains of two or more endolysins have been swapped/exchanged do qualify as "muralytic enzymes" just as truncated endolysins, in which only the enzymatic active domain remains. The activity, in particular of endolysins, can be measured by assays well known in the art by a person skilled in the art as e.g. antibacterial assays which are e.g. described in Briers et al. (J. Biochem. Biophys Methods; 2007; 70: 531-533) or Donovan et al. (J. FEMS Microbiol Lett. 2006 December; 265(1)) (both incorporated herein by reference) and similar publications.

The term "endolysin" as used herein refers to a bacteriophage-derived enzyme which is suitable to catalyze the cleavage (in particular by hydrolysis) of bacterial cell walls. Preferably, endolysins are bacteriophage-derived enzymes which are synthesized by the virus using late gene expression in the lytic cycle of phage multiplication and mediate the release of progeny virions. Endolysins typically exhibit at least one of the following activities: endopeptidase, chitinase, T4 like muraminidase, lambda like muraminidase, N-acetyl-muramoyl-L-alanine-amidase (amidase), muramoyl-L-alanine-amidase, muramidase, lytic transglycosylase (C), lytic transglycosylase (M), N-acetyl-muramidase (lysozyme), N-acetyl-glucosaminidase or transglycosylases as e.g. KZ144 endolysin. In some endolysins, this activity manifests in an individual "enzymatically active domain" (EAD). In addition, the endolysins may contain also regions which are enzymatically inactive, and bind to the cell wall of the host bacteria, the so-called CBDs (cell wall binding domains). The term "endolysin" also encompasses enzymes which comprise modifications and/or alterations vis-a-vis naturally occurring endolysins. Such alterations and/or modifications may comprise mutations such as deletions, insertions and additions, substitutions or combinations thereof and/or chemical changes of the amino acid residues. Particularly preferred chemical changes are biotinylation, acetylation, pegylation, chemical changes of the amino-, SH- or carboxyl-groups. Said endolysins exhibit on a general level the lytic activity of the respective wild-type endolysin. However, said activity can be the same, higher or lower as the activity of the respective wild-type endolysin. Said activity can be for example at least about 50, 60, 70, 80, 90, 100, 110, 120, 130, 140, 150, 160, 170, 180, 190 or at least about 200% of the activity of the respective wild-type endolysin or even more. The activity can be measured by assays well known in the art by a person skilled in the art as e.g. the plate lysis assay or the liquid lysis assay which are e.g. described in Briers et al. (J. Biochem. Biophys Methods; 2007; 70: 531-533) or Donovan et al. (J. FEMS Microbiol Lett. 2006 December; 265(1) (both incorporated herein by reference) and similar publications.

The term "Gram negative endolysin" refers to endolysins deriving from bacteriophages targeting Gram negative bacteria. These endolysins are capable of degrading the peptidoglycan of the respective (host) bacteria.

A "modular" endolysin, as used herein, is an endolysin which exhibits at least two distinct functional domains, namely at least one "enzymatically active domain" (EAD) and at least one "cell-wall-binding domain" (CBD). While the former provides the actual enzymatic activity, the latter may provide for target binding. Due to their domain character, these two activities can be separated from each other. Endolysins lacking a distinct CBD do not fall under the term "modular endolysin".

The term "bacteriophage tail/baseplate protein" is generally understood be a person skilled in the art. Tail proteins and baseplate proteins are proteins of bacteriophages. Binding structures located in the tail fiber and/or baseplate of bacteriophages play an important role in mediating injection of the phage genome into the host cell. Tail fiber proteins are positioned at the tip of the tail and are responsible for binding to the cell surface by recognizing a potential host bacterium and attaching to its outer surface. Baseplate proteins control the transfer of the genetic material and can have also cell binding properties. Especially for Myoviruses of Gram negative bacteria (e.g. T4 or P2 phages) different motifs are described which show homology to peptidoglycan binding domains like LysM. Another example is the gp5 of the ICP1 *vibrio* phage and related proteins encoded in the genome of phages infecting different species like e.g. *Methylobacter* sp. These consist of a peptidoglycan binding domain and an enzymatic active domain, able to degrade the murein layer of the host bacteria.

The term, "antimicrobial peptide" (AMP) as used herein refers preferably to any peptide that has microbicidal and/or microbistatic activity on, for example, bacteria, viruses, fungi, yeasts, *mycoplasma* and protozoa. In some embodiments, the peptide will be a naturally occurring peptide. In other embodiments, the peptide will be an artificial peptide not occurring in nature. For example, the antimicrobial peptide may be a mutated version of naturally occurring peptide. The term "antimicrobial peptide" as used herein refers in particular to any peptide having anti-bacterial, anti-fungal, anti-mycotic, anti-parasitic, anti-protozoal, anti-viral, anti-infectious, anti-infective and/or germicidal, algicidal, amoebicidal, microbicidal, bactericidal, fungicidal, parasiticidal, protozoacidal, protozoicidal properties. Preferred are anti-bacterial peptides. The antimicrobial peptide may be a member of the RNase A super family, a defensin, cathelicidin, granulysin, histatin, psoriasin, dermicidine or hepcidin. The antimicrobial peptide may be naturally occurring in insects, fish, plants, arachnids, vertebrates or mammals. Preferably the antimicrobial peptide may be naturally occurring in radish, silk moth, wolf spider, frog, preferably in *Xenopus laevis, Rana* frogs, more preferably in *Rana catesbeiana*, toad, preferably Asian toad *Bufo bufo garizans*, fly, preferably in *Drosophila*, more preferably in *Drosophila melanogaster*, in *Aedes aegypti*, in honey bee, bumblebee, preferably in *Bombus pascuorum*, flesh fly, preferably in *Sarcophaga peregrine*, scorpion, horseshoe crab, catfish, preferably in *Parasilurus asotus*, cow, pig, sheep, porcine, bovine, monkey and human. As used herein, an "antimicrobial peptide" (AMP) may in particular be a peptide which is not a cationic peptide, polycationic peptide, amphipathic peptide, sushi peptide or defensins, but nevertheless exhibits antimicrobial activity. Examples of antimicrobial peptides may be found in "The Antimicrobial Peptide Database" of the University of Nebraska Medical Center (Omaha, Nebr., USA aps.unmc.edu/AP/main.php).

The term "amphipathic peptide" as used herein refers to synthetic peptides having both hydrophilic and hydrophobic functional groups. Preferably, the term "amphipathic peptide" as used herein refers to a peptide having a defined arrangement of hydrophilic and hydrophobic groups.

As used herein, the term "cationic peptide" refers to a peptide having positively charged amino acid residues. Preferably a cationic peptide has a pKa-value of 9.0 or greater. Typically, at least four of the amino acid residues of the cationic peptide can be positively charged, for example, lysine or arginine. "Positively charged" refers to the side chains of the amino acid residues which have a net positive charge at about physiological conditions. The term "cationic peptide" as used herein refers also to polycationic peptides, but also includes cationic peptides which comprise for example less than 20%, preferably less than 10% positively charged amino acid residues.

The term "polycationic peptide" as used herein refers preferably to a peptide composed of mostly positively charged amino acid residues, in particular lysine and/or arginine residues. A peptide is composed of mostly positively charged amino acid residues if at least about 60, 70, 75, 80, 85, 90, 95 or about 100% of the amino acid residues are positively charged amino acid residues, in particular lysine and/or arginine residues. The amino acid residues being not positively charged amino acid residues can be neutrally charged amino acid residues and/or negatively charged amino acid residues and/or hydrophobic amino acid residues. Preferably the amino acid residues being not positively charged amino acid residues are neutrally charged amino acid residues, in particular serine and/or glycine.

The term "sushi peptide" as used herein refers to complement control proteins (CCP) having short consensus repeats. The sushi module of sushi peptides functions as a protein-protein interaction domain in many different proteins. Peptides containing a Sushi domain have been shown to have antimicrobial activities. Preferably, sushi peptides are naturally occurring peptides.

The term "defensin" as used herein refers to a peptide present within animals, preferably mammals, more preferably humans, wherein the defensin plays a role in the innate host defense system as the destruction of foreign substances such as infectious bacteria and/or infectious viruses and/or fungi. A defensin is a non-antibody microbicidal and/or tumoricidal protein, peptide or polypeptide. Examples for "defensins" are "mammalian defensins," alpha-defensins, beta-defensins, indolicidin and magainins. The term "defensins" as used herein refers both to an isolated form from animal cells or to a synthetically produced form, and refers also to variants which substantially retain the cytotoxic activities of their parent proteins, but whose sequences have been altered by insertion or deletion of one or more amino acid residues.

As used herein, the term "tag" refers to an amino acid sequence, which is typically in the art fused to or included in another amino acid sequence for a) improving expression of the overall amino acid sequence or polypeptide, b) facilitating purification of the overall amino acid sequence or polypeptide, c) facilitating immobilisation of the overall amino acid sequence or polypeptide, and/or d) facilitating detection of the overall amino acid sequence or polypeptide. Examples for tags are His tags, such as His5-tags, His6-tags, His7-tags, His8-tags, His9-tags, His10-tags, His11-tags, His12-tags, His16-tags and His20-tags, Strep-tags, Avi-tags, Myc-tags, GST-tags, JS-tags, cystein-tags, FLAG-tags, HA-tags, thioredoxin or maltose binding proteins (MBP), CAT, GFP, YFP, etc. The person skilled in the art will know a vast number of tags suitable for different technical applications. The tag may for example make such tagged polypeptide suitable for e.g. antibody binding in different ELISA assay formats or other technical applications.

As used herein, the term "% sequence identity", has to be understood as follows: Two sequences to be compared are aligned to give a maximum correlation between the sequences. This may include inserting "gaps" in either one or both sequences, to enhance the degree of alignment. A % identity may then be determined over the whole length of each of the sequences being compared (so-called global alignment), that is particularly suitable for sequences of the same or similar length, or over shorter, defined lengths (so-called local alignment), that is more suitable for sequences of unequal length. In the above context, an amino acid sequence having a "sequence identity" of at least, for example, 95% to a query amino acid sequence, is intended to mean that the sequence of the subject amino acid sequence is identical to the query sequence except that the subject amino acid sequence may include up to five amino acid alterations per each 100 amino acids of the query amino acid sequence. In other words, to obtain an amino acid sequence having a sequence of at least 95% identity to a query amino acid sequence, up to 5% (5 of 100) of the amino acid residues in the subject sequence may be inserted or substituted with another amino acid or deleted. Methods for comparing the identity and homology of two or more sequences are well known in the art. The percentage to which two sequences are identical can for example be determined by using a mathematical algorithm. A preferred, but not limiting, example of a mathematical algorithm which can be used is the algorithm of Karlin et al. (1993), PNAS USA, 90:5873-5877. Such an algorithm is integrated in the BLAST family of programs, e.g. BLAST or NBLAST program (see also Altschul et al., 1990, J. Mol. Biol. 215, 403-410 or Altschul et al. (1997), Nucleic Acids Res, 25:3389-3402), accessible through the home page of the NCBI at world wide web site ncbi.nlm.nih.gov) and FASTA (Pearson (1990), Methods Enzymol. 83, 63-98; Pearson and Lipman (1988), Proc. Natl. Acad. Sci. U.S.A 85, 2444-2448.). Sequences which are identical to other sequences to a certain extent can be identified by these programmes. Furthermore, programs available in the Wisconsin Sequence Analysis Package, version 9.1 (Devereux et al, 1984, Nucleic Acids Res., 387-395), for example the programs BESTFIT and GAP, may be used to determine the % identity between two polypeptide sequences. BESTFIT uses the "local homology" algorithm of (Smith and Waterman (1981), J. Mol. Biol. 147, 195-197.) and finds the best single region of similarity between two sequences. If herein reference is made to an amino acid sequence sharing a particular extent of sequence identity to a reference sequence, then said difference in sequence is preferably due to conservative amino acid substitutions. Preferably, such sequence retains the activity of the reference sequence, e.g. albeit maybe at a slower rate. In addition, if reference is made herein to a sequence sharing "at least" at certain percentage of sequence identity, then 100% sequence identity are preferably not encompassed.

The term "comprising", as used herein, shall not be construed as being limited to the meaning "consisting of" (i.e. excluding the presence of additional other matter). Rather, "comprising" implies that optionally additional matter may be present. The term "comprising" encompasses as particularly envisioned embodiments falling within its scope "consisting of" (i.e. excluding the presence of additional other matter) and "comprising but not consisting of" (i.e. requiring the presence of additional other matter), with the former being more preferred.

The use of the word "a" or "an", when used herein, may mean "one," but it is also consistent with the meaning of "one or more," "at least one," and "one or more than one."

The present invention relates in a first aspect to a polypeptide comprising a Gram negative endolysin and a peptide selected from the group consisting of an antimicrobial peptide, an amphipathic peptide, a cationic peptide, a hydrophobic peptide, a sushi peptide or a defensin, wherein the endolysin is selected from the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, and sequences having at least 80% sequence identity with SEQ ID NO:1, SEQ ID NO:2, SEQ ID NO:3, SEQ ID NO:4, SEQ ID NO:5, SEQ ID NO:6, SEQ ID NO:7, SEQ ID NO:8 and/or SEQ ID NO:9, and preferably with the provisos that
a) the polypeptide does not comprise the sequence according to SEQ ID NO:10,
b) the peptide is selected from the group consisting of an antimicrobial peptide, an amphipathic peptide, a sushi peptide or a defensin, if the polypeptide comprises the sequence of SEQ ID NO:4,
c) the polypeptide does not comprise a cell wall binding domain of i) a modular Gram-negative endolysin or ii) a bacteriophage tail/baseplate protein, if the endolysin has a sequence according to:

| Host | Phage name | Protein ID |
| --- | --- | --- |
| *Escherichia* | Enterobacteria phage CC31 | YP_004009990.1 | or a corresponding sequences merely lacking in addition the N-terminal methionine.

In a second aspect the present invention relates to a polypeptide comprising a Gram negative endolysin and a peptide selected from the group consisting of an antimicrobial peptide, an amphipathic peptide, a cationic peptide, a hydrophobic peptide, a sushi peptide or a defensin, wherein the endolysin in turn is an endolysin selected from the group consisting of SEQ ID NO:7, SEQ ID NO:8, SEQ ID NO:9 and sequences having at least 80% sequence identity with SEQ ID NO:7, SEQ ID NO:8, and/or SEQ ID NO:9, and wherein the endolysin does not comprise any cysteine residue in its sequence.

The absence of any cysteine residue in the endolysin sequence may be because already the wildtype form of the endolysin does not comprise such cysteine residue or because any cysteine residues occurring in the wildtype sequence have been technically modified/mutated (e.g. C→S, or C→A or C→G, preferably C→S), for instance to increase stability and to reduce aggregation.

In a third aspect the present invention relates to a polypeptide comprising a Gram negative endolysin and a peptide selected from the group consisting of an antimicrobial peptide, an amphipathic peptide, a cationic peptide, a sushi peptide or a defensin, wherein the endolysin in turn is an endolysin selected from the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, and sequences having at least 80% sequence identity with SEQ ID NO:1, SEQ ID NO:2, SEQ ID NO:3, SEQ ID NO:4, SEQ ID NO:5, SEQ ID NO:6, SEQ ID NO:7, SEQ ID NO:8 and/or SEQ ID NO:9, and wherein the peptide is positioned within the polypeptide N-terminally of the endolysin (for instance in embodiments wherein the endolysin constitutes the most C-terminal component of the polypeptide).

In the following, the polypeptide of the invention (be it now of the first, second or third aspect of the invention) will be discussed in more detail. It is understood that anything set forth below applies equally to all three of the aspects above, unless explicitly stated otherwise.

The endolysin derives from a phage infecting Gram negative bacteria, i.e. is a Gram negative endolysin. Examples of endolysins for use in the inventive polypeptide are for instance the endolysins of *Citrobacter koseri* phage CkP1 (SEQ ID NO:1) or the endolysin of Enterobacteria phage CC31 (SEQ ID NO:2) or the endolysin of *Serratia* phage CHI14 (SEQ ID NO:3), or sequences sharing at least 80% sequence identity, preferably at least 85% sequence identity, more preferably at least 90% sequence identity, more preferably at least 95% sequence identity, more preferably at least 96% sequence identity, more preferably at least 97% sequence identity, more preferably at least 98% sequence identity, more preferably at least 99% sequence identity with SEQ ID NO:1, SEQ ID NO:2 and/or SEQ ID NO:3, in particular with SEQ ID NO:1 and/or SEQ ID NO:2. For example, modified versions of these endolysins, with a C54S mutation and/or lacking the N-terminal methionine, are preferred forms of endolysin to be used as component of the inventive polypeptide (see for instance SEQ ID NO:4, subject to the disclaimer above, SEQ ID NO:5, SEQ ID NO:6, SEQ ID NO:7, SEQ ID NO:8, and SEQ ID NO:9, which are particularly preferred embodiments). Particularly preferred endolysin sequences are thus also SEQ ID NO:4, SEQ ID NO:5, SEQ ID NO:6, SEQ ID NO:7, SEQ ID NO:8, or SEQ ID NO:9, or a sequence having at least 80% sequence identity, preferably at least 85% sequence identity, more preferably at least 90% sequence identity, more preferably at least 95% sequence identity, more preferably at least 96% sequence identity, more preferably at least 97% sequence identity, more preferably at least 98% sequence identity, more preferably at least 99% sequence identity with SEQ ID NO:4 (subject to the proviso above), SEQ ID NO:5, SEQ ID NO:6, SEQ ID NO:7, SEQ ID NO:8, and/or SEQ ID NO:9, in particular with SEQ ID NO:4, SEQ ID NO:5, SEQ ID NO:7 and/or SEQ ID NO:8.

As mentioned previously, it is meanwhile established for about a decade that Gram negative bacteria can be killed with respective Gram negative endolysins even if added from without, if the endolysins are fused with, e.g., an antimicrobial peptide, an amphipathic peptides or a cationic peptide (see for example WO 2010/023207, WO 2010/149792, WO 2011/134998, WO 2012/146738, or WO 2015/121443, all incorporated herein by reference). In the following, this peptide within the inventive polypeptide will also be referred to as "peptide component". It is understood that this peptide component, as used herein, is not a conventional tag like His-tags, such as His5-tags, His6-tags, His7-tags, His8-tags, His9-tags, His10-tags, His11-tags, His12-tags, His16-tags and His20-tags, Strep-tags, Avi-tags, Myc-tags, Gst-tags, JS-tags, cystein-tags, FLAG-tags or other tags known in the art, such as thioredoxin or maltose binding proteins (MBP).

Preferred cationic and/or polycationic peptides are those comprising at least one motive according to SEQ ID NO:11 (KRKKRK). In particular cationic amino acid sequence stretches comprising at least 2, 3, 4, 5, 6, 7, 8, 9, 10, 11, 12, 13, 14, 15, 16 or 17 motives according to SEQ ID NO: 11 (KRKKRK) are preferred. More preferred are cationic peptide stretches comprising at least one KRK motive (lys-arg-lys), preferable at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32 or 33 KRK motives.

In another preferred embodiment of the present invention the cationic peptide comprises beside the positively charged amino acid residues, in particular lysine and/or arginine residues, neutrally charged amino acid residues, in particular glycine and/or serine residues. Preferred are cationic amino acid sequence stretches consisting of about 70% to about 100%, or about 80% to about 95%, or about 85% to about 90% positively charged amino acid residues, in particular lysine, arginine and/or histidine residues, more preferably lysine and/or arginine residues and of about 0% to about 30%, or about 5% to about 20%, or about 10% to about 20% neutrally charged amino acid residues, in particular glycine and/or serine residues. Preferred are amino acid sequence stretches consisting of about 4% to about 8% serine residues, of about 33% to about 36% arginine residues and of about 56% to about 63% lysine residues. Especially preferred are amino acid sequence stretches comprising at least one motive according to SEQ ID NO: 12 (KRXKR), wherein X is any other amino acid than lysine, arginine and histidine. Especially preferred are polypeptide stretches comprising at least one motive according to SEQ ID NO: 13 (KRSKR). More preferred are cationic stretches comprising at least about 2, 3, 4, 5, 6, 7, 8, 9, 10, 11, 12, 13, 14, 15, 16, 17, 18, 19 or at least about 20 motives according to SEQ ID NO: 12 (KRXKR) or SEQ ID NO: 13 (KRSKR).

Also preferred are cationic amino acid sequence stretches consisting of about 9 to about 16% glycine residues, of about 4 to about 11% serine residues, of about 26 to about 32% arginine residues and of about 47 to about 55% lysine residues. Especially preferred are amino acid sequence stretches comprising at least one motive according to SEQ ID NO: 14 (KRGSG). More preferred are cationic stretches comprising at least about 2, 3, 4, 5, 6, 7, 8, 9, 10, 11, 12, 13, 14, 15, 16, 17, 18, 19 or at least bout 20 motives according to SEQ ID NO: 14 (KRGSG).

In another preferred embodiment of the present invention such cationic amino acid sequence stretch comprises beside the positively charged amino acid residues, in particular lysine and/or arginine residues, hydrophobic amino acid residues, in particular valine, isoleucine, leucine, methionine, phenylalanine, tryptophan, cysteine, alanine, tyrosine, proline and glycine residues, more preferably alanine, valine, leucine, isoleucine, phenylalanine, and/or tryptophan residues. Preferred are cationic amino acid sequence stretches consisting of about 70% to about 100%, or about 80% to about 95%, or about 85% to about 90% positively charged amino acid residues, in particular lysine and/or arginine residues and of about 0% to about 30%, or about 5% to about 20%, or about 10% to about 20% hydrophobic amino acid residues, valine, isoleucine, leucine, methionine, phenylalanine, tryptophan, cysteine, alanine, tyrosine, proline and glycine residues, more preferably alanine, valine, leucine, isoleucine, phenylalanine, and/or tryptophan residues. Examples for cationic and polycationic amino acid sequence stretches are listed in the following table:

TABLE 1

| amino acid sequence stretch | length | SEQ ID NO: |
|---|---|---|
| KRKKRK | 6 | 11 |
| KRKKRKKRK | 9 | 15 |
| RRRRRRRRR | 9 | 16 |
| KKKKKKKK | 8 | 17 |
| KRKKRKKRKK | 10 | 18 |
| KRKKRKKRKKRK | 12 | 19 |
| KRKKRKKRKKRKKR | 14 | 20 |
| KKKKKKKKKKKKKKKK | 16 | 21 |
| KRKKRKKRKKRKKRKKRK | 18 | 22 |
| KRKKRKKRKKRKKRKKRKK | 19 | 23 |
| RRRRRRRRRRRRRRRRRRR | 19 | 24 |

TABLE 1-continued

| amino acid sequence stretch | length | SEQ ID NO: |
|---|---|---|
| KKKKKKKKKKKKKKKKKKK | 19 | 25 |
| KRKKRKKRKRSKRKKRKKRK | 20 | 26 |
| KRKKRKKRKRSKRKKRKKRKK | 21 | 27 |
| KRKKRKKRKRKKRKKRKKRK | 21 | 28 |
| KRKKRKKRKRGSGKRKKRKKRK | 22 | 29 |
| KRKKRKKRKRGSGSGKRKKRKKRK | 24 | 30 |
| KRKKRKKRKRKRKRKKRKKRKKRKK | 25 | 31 |
| KRKKRKKRKRSKRKKRKKRKRSKRKKRKKRK | 31 | 32 |
| KRKKRKKRKRGSGSGKRKKRKKRKGSGSGKRKKRKKRK | 38 | 33 |
| KRKKRKKRKRKRKKRKKRKKRKKRKKRKKRKRKKRKKRK | 39 | 34 |
| KRKKRKKRKRSKRKKRKKRKRSKRKKRKKRKRSKRKKRKKRK | 42 | 35 |

In a further aspect of the present invention the peptide is an antimicrobial peptide, which comprises a positive net charge and around 50% hydrophobic amino acids. The antimicrobial peptides are amphipathic with a length of about 12 to about 50 amino acid residues. The antimicrobial peptides are naturally occurring in insects, fish, plants, arachnids, vertebrates or mammals. Preferably the antimicrobial peptide may be naturally occurring in radish, silk moth, wolf spider, frog, preferably in *Xenopus laevis*, *Rana* frogs, more preferably in *Rana catesbeiana*, toad, preferably Asian toad *Bufo bufo gargarizans*, fly, preferably in *Drosophila*, more preferably in *Drosophila melanogaster*, in *Aedes aegypti*, in honey bee, bumblebee, preferably in *Bombus pascuorum*, flesh fly, preferably in *Sarcophaga peregrina*, scorpion, horseshoe crab, catfish, preferably in *Parasilurus asotus*, cow, pig, sheep, porcine, bovine, monkey and human.

In another preferred embodiment of the present invention the antimicrobial peptide consists of about 10% to about 35% or about 15% to about 45%, or about 20% to about 45% positively charged amino acid residues, in particular lysine and/or arginine residues and of about 50% to about 80%, or about 60% to about 80%, or about 55% to about 75%, or about 70% to about 90% hydrophobic amino acid residues, valine, isoleucine, leucine, methionine, phenylalanine, tryptophan, cysteine, alanine, tyrosine, proline and glycine residues, more preferably alanine, valine, leucine, isoleucine, phenylalanine, and/or tryptophan residues.

In another preferred embodiment of the present invention the antimicrobial peptide consist of about 4% to about 58% positively charged amino acid residues, in particular lysine and/or arginine residues and of about 33% to about 89% hydrophobic amino acid residues, valine, isoleucine, leucine, methionine, phenylalanine, tryptophan, cysteine, alanine, tyrosine, proline and glycine residues, more preferably alanine, valine, leucine, isoleucine, phenylalanine, and/or tryptophan residues.

Examples for antimicrobial amino acid sequences which may be used in carrying out the present invention are listed in the following table.

TABLE 2

| Peptide | Sequence | SEQ ID NO |
|---|---|---|
| LL-37 | LLGDFFRKSKEKIGKEFKRIVQRIKDFLRNLVPRTES | 36 |
| SMAP-29 | RGLRRLGRKIAHGVKKYGPTVLRIIRIAG | 37 |
| Indolicidin | ILPWKWPWWPWRR | 38 |
| Protegrin | RGGRLCYCRRRFCVCVGR | 39 |
| Cecropin P1 | SWLSKTAKKLENSAKKRISEGIAIAIQGGPR | 40 |
| Magainin | GIGKFLHSAKKFGKAFVGEIMNS | 41 |
| Pleurocidin | GWGSFFKKAAHVGKHVGKAALTHYL | 42 |
| Cecropin A (*A. aegypti*) | GGLKKLGKKLEGAGKRVFNAAEKALPVVAGAKALRK | 43 |
| Cecropin A (*D. melanogaster*) | GWLKKIGKKIERVGQHTRDATIQGLGIPQQAANVAATARG | 44 |
| Buforin II | TRSSRAGLQFPVGRVHRLLRK | 45 |
| Sarcotoxin IA | GWLKKIGKKIERVGQHTRDATIQGLGIAQQAANVAATAR | 46 |
| Apidaecin | ANRPVYIPPPRPPHPRL | 47 |
| Ascaphine 5 | GIKDWIKGAAKKLIKTVASHIANQ | 48 |
| Nigrocine 2 | GLLSKVLGVGKKVLCGVSGLVC | 49 |
| Pseudin 1 | GLNTLKKVFQGLHEAIKLINNHVQ | 50 |
| Ranalexin | FLGGLIVPAMICAVTKKC | 51 |
| Melittin | GIGAVLKVLTTGLPALISWIKRKRQQ | 52 |

TABLE 2-continued

| Peptide | Sequence | SEQ ID NO |
|---|---|---|
| Lycotoxin 1 | IWLTALKFLGKHAAKKLAKQQLSKL | 53 |
| Parasin 1 | KGRGKQGGKVRAKAKTRSS | 54 |
| Buforin I | AGRGKQGGKVRAKAKTRSSRAGLQFPVGRVHRLLRKGNY | 55 |
| Dermaseptin 1 | ALWKTMLKKLGTMALHAGKAALGAAADTISQGTQ | 56 |
| Bactenecin 1 | RLCRIVVIRVCR | 57 |
| Thanatin | GSKKPVPIIYCNRRTGKCQRM | 58 |
| Brevinin 1T | VNPIILGVLPKVCLITKKC | 59 |
| Ranateurin 1 | SMLSVLKNLGKVGLGFVACKINIKQC | 60 |
| Esculentin 1 | GIFSKLGRKKIKNLLISGLKNVGKEVGMDVVRTGIKIAGCKIKGEC | 61 |
| Tachyplesin | RWCFRVCYRGICYRKCR | 62 |
| Androctonin | RSVCRQIKICRRGGCYYKCTNRPY | 63 |
| alpha-defensin | DCYCRIPACIAGERRYGTCIYQGRLWAFCC | 64 |
| beta-defensin | NPVSCVRNKGICVPIRCPGSMKQIGTCVGRAVKCCRKK | 65 |
| theta-defensin | GFCRCLCRRGVCRCICTR | 66 |
| defensin (sapecin A) | ATCDLLSGTGINHSACAAHCLLRGNRGGYCNGKAVCVCRN | 67 |
| Thionin (crambin) | TTCCPSIVARSNFNVCRIPGTPEAICATYTGCIIIPGATCPGDYAN | 68 |
| defensin from radish | QKLCQRPSGTWSGVCGNNNACKNQCIRLEKARHGSCNYVFPAHCICYFPC | 69 |
| Cathelecidin-BF | KFFRKLKKSVKKRAKEFFKKPRVIGVSIPF | 70 |
| Drosomycin | DCLSGRYKGPCAVWDNETCRRVCKEEGRSSGHCSPSLKCWCEGC | 71 |
| Hepcidin | DTHFPICIFCCGCCHRSKCGMCCKT | 72 |
| Bac 5 | RFRPPIRRPPIRPPFYPPFRPPIRPPIFPPIRPPFRPPLGRPFP | 73 |
| PR-39 | RRRPRPPYLPRPRPPPFFPPRLPPRIPPGFPPRFPPRFP | 74 |
| Pyrrhocoricin | VDKGSYLPRPTPPRPIYNRN | 75 |
| Histatin 5 | DSHAKRHHGYKRKFHEKHHSHRGY | 76 |
| ECP19 | RPPQFTRAQWFAIQHISLN | 77 |
| MSI-594 | GIGKFLKKAKKGIGAVLKVLTTG | 78 |
| TL-ColM | METLTVHAPSPSTNLPSYGNGAFSLSAPHVPGAGP | 79 |
| SBO | KLKKIAQKIKNFFAKLVA | 80 |

A particularly preferred antimicrobial peptide for use in the inventive polypeptide of the present invention is SMAP-29 (SEQ ID NO:37).

Further particularly preferred antimicrobial peptides are peptides according to SEQ ID NO: 70 and SEQ ID NO:81.

In a further embodiment the peptide component of the inventive polypeptide may be a sushi peptide which is described by Ding J L, Li P, Ho B Cell Mol Life Sci. 2008 April; 65(7-8):1202-19. The Sushi peptides: structural characterization and mode of action against Gram-negative bacteria. Especially preferred is the sushi 1 peptide according to SEQ ID NO: 82. Preferred sushi peptides are sushi peptides S1 and S3 and multiples thereof; Tan et al. FASEB J. 2000 September; 14(12):1801-13.

In a further aspect of the present invention the peptide component is an amphipathic peptide, which comprises one or more of the positively charged amino acid residues of lysine, arginine and/or histidine, combined to one or more of the hydrophobic amino acid residues of valine, isoleucine, leucine, methionine, phenylalanine, tryptophan, cysteine, alanine, tyrosine, proline and/or glycine. Side chains of the amino acid residues are oriented in order that cationic and hydrophobic surfaces are clustered at opposite sides of the peptide. Preferably, more than about 30, 40, 50, 60 or 70% of the amino acids in said peptide are positively charged amino acids. Preferably, more than about 30, 40, 50, 60 or 70%, of the amino acid residues in said peptide are hydrophobic amino acid residues. Advantageously, the amphipathic peptide is present at the N-terminal (most preferred) or the C-terminal end of the polypeptide according to the present invention.

In another embodiment of the invention, the amphipathic peptide consists of at least 5, more preferably at least of 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or at least 50 amino acid residues. In a preferred embodiment at least about 30, 40, 50, 60 or 70% of said amino acid residues of the amphipathic peptide are either arginine or lysine residues and/or at least about 30, 40, 50, 60 or 70% of said amino acid residues of the amphipathic peptide are of the hydrophobic amino acids valine, isoleucine, leucine, methionine, phenylalanine, tryptophan, cysteine, alanine, tyrosine, proline and/or glycine.

In another preferred embodiment of the present invention the amphipathic peptide stretch comprises beside the positively charged amino acid residues, in particular lysine and/or arginine residues, hydrophobic amino acid residues, in particular valine, isoleucine, leucine, methionine, phenylalanine, tryptophan, cysteine, alanine, tyrosine, proline and glycine residues, more preferably alanine, valine, leucine, isoleucine, phenylalanine, and/or tryptophan residues. Preferred are amphipathic peptide stretches consisting of about 10% to about 50%, or about 20% to about 50%, or about 30% to about 45% or about 5% to about 30% positively charged amino acid residues, in particular lysine and/or arginine residues and of about 50% to about 85%, or about 50% to about 90%, or about 55% to about 90%, or about 60% to about 90%, or about 65% to about 90% hydrophobic amino acid residues, valine, isoleucine, leucine, methionine, phenylalanine, tryptophan, cysteine, alanine, tyrosine, proline and glycine residues, more preferably alanine, valine, leucine, isoleucine, phenylalanine, and/or tryptophan residues. In another preferred embodiment amphipathic peptide stretches consisting of 12% to about 50% positively charged amino acid residues, in particular lysine and/or arginine residues and of about 50% to about 85% hydrophobic amino acid residues, valine, isoleucine, leucine, methionine, phenylalanine, tryptophan, cysteine, alanine, tyrosine, proline and glycine residues, more preferably alanine, valine, leucine, isoleucine, phenylalanine, and/or tryptophan residues.

Preferred amphipathic peptides are WLBU2-Variant having the amino acid sequence according to SEQ ID NO: 83 and Walmagh 2 according to SEQ ID NO: 84.

In a particularly preferred embodiment of the present invention, the peptide (within the inventive polypeptide) comprises a sequence motif which:

i) is 16, 17, 18, 19 or 20 amino acids in length;

ii) comprises at least 40% and at most 60% amino acids selected from a first group of amino acids consisting of lysine, arginine and histidine,
wherein each amino acid is selected independently from said first group,
wherein each amino acid selected from this first group is arranged in said sequence motif either alone, pairwise together with a further amino acid selected from the first group, or in a block with 2 further amino acids selected from the first group, but does not occur in a block with 3 or more amino acids selected from the first group, wherein at least 2 pairs of amino acids selected from the first group are present in said sequence motif, and wherein at most one block with 3 of the amino acids selected from the first group in a row is present in said sequence motif, with the additional proviso, that if such block with 3 amino acids of the first group is present in said sequence motif, then the amino acids at positions 12, −11, −8, −5, −4, +6, +7, +10, +13, and +14 relative to the first amino acid of the 3 amino acid block are—provided the respective position may be found in said sequence motif—not selected from said first group, iii) comprises at least 40% and at most 60% amino acids selected from a second group of amino acids consisting of alanine, glycine, isoleucine, leucine, phenylalanine, serine, threonine, tryptophan, tyrosine and valine,
wherein each amino acid is selected independently from said second group,
wherein preferably at least three different amino acids are selected from this second group, if the sum of amino acids selected from the first group and selected from the second group yield 100% of the sequence motif;
wherein preferably the sequence motif does not comprise the sequence AFV, if the sequence motif contains at least two single, non-adjacent phenylalanine residues and at least one of these phenylalanine residues is directly preceded by a lysine residue, and
wherein the sequence motif does preferably not comprise the sequence AALTH (SEQ ID NO:85), if the sequence motif contains at least three non-adjacent histidine residues, iv) wherein the remaining amino acids of said sequence motif, if any are present in the motif, are selected from a third group consisting of asparagine, aspartic acid, glutamine, glutamic acid, methionine, or cysteine, wherein each of said amino acids is selected independently from said third group, and wherein glutamine may be preferably selected only once and wherein the selection may preferably furthermore not comprise a combination of glutamine and glutamic acid.

The sequence motif defined above in i) to iv) may represent only a part of the peptide component of the inventive polypeptide, i.e. the peptide component of the inventive polypeptide is longer than the sequence motif.

Alternatively, the sequence motif may be the sequence of the peptide component, i.e. the sequence of the peptide component in the inventive polypeptide is identical to the sequence of the sequence motif. Moreover, and as will be apparent from the example provided in FIG. 1, it is possible that the inventive polypeptide comprises one or more such sequence motifs. For instance, the 20mer motif may inherently comprise a 16mer motif also complying with the criteria set out above. The fact, that the peptide component of the inventive polypeptide comprises "a" sequence motif as defined above may thus not be understood as meaning that the inventive polypeptide may only comprise "one" sequence motif and no further (e.g. overlapping) sequence motifs also complying with the limits set out above.

The sequence motif of the peptide component of the inventive polypeptide may be 16, 17, 18, 19 or 20 amino acids in length. Preferably, the sequence motif is 17, 18 or 19 amino acids in length, even more preferably 17 or 18 amino acids in length.

The sequence motif of the peptide component of the inventive polypeptide comprises at least 40% and at most 60% amino acids selected from a first group of amino acids. Said first group consists of lysine, arginine and histidine. If the sequence motif is 16 amino acids long, it will exhibit at least 7 and at most 9 amino acids selected from this first group. If the sequence motif is 17 amino acids long, it will exhibit at least 7 and at most 10 amino acids selected from this first group. If the sequence motif is 18 amino acids long, it will exhibit at least 8 and at most 10 amino acids selected from this first group. If the sequence motif is 19 amino acids long, it will exhibit at least 8 and at most 11 amino acids selected from this first group. If the sequence motif is 20 amino acids long, it will exhibit at least 8 and at most 12 amino acids selected from this first group.

Preferred amino acids for selection within this first group are lysine and arginine. Preferably, the sequence motif does not comprise more than 50% histidine residues. Even more preferably, the sequence motif does not comprise more than 25% histidine residues. In some embodiments of the invention, the sequence motif comprises only one or even no histidine residue.

The amino acids selected from the first group are selected independently. This implies, for example, that if a given sequence motif comprises, e.g., eight amino acids selected from the first group, that each of these eight amino acid residues can be selected independently from previous or subsequent selections from said first group. The selected amino acids may thus comprise all three types of amino acids (lysine, arginine, and histidine), may be identical (e.g. 8 lysine or 8 arginine residues, respectively), or may comprise only two of the three types of amino acids (e.g. lysine and arginine). Likewise, independent selection does not prescribe any specific ratio between the individually selected amino acids. For example, and without being limited thereto, 8 amino acids selected from this first group may be 8 lysine residues, 7 arginine residues and 1 histidine residue or 3 arginine, 4 lysine and 1 histidine residue.

The positioning of the amino acid residues selected from the first group within the sequence motif is subject to certain limitations. Each amino acid selected from this first group may only be arranged in said sequence motif either alone, pairwise together with a further amino acid selected from the first group, or in a block with 2 further amino acids selected from the first group.

"Alone" means that an amino acid selected from said first group, e.g. lysine (K), is neither N-terminally nor C-terminally flanked by another amino acid from said first group. Adjacent amino acid residues may be selected from the second or, as the case may be, from the third group (e.g. LKE, N-KE (at N-terminus of motif), LK-C (at C-terminus of motif)). Noteworthy, potential further amino acids within the inventive polypeptide, but outside of the sequence motif, are not taken into account for this positional determination. An amino acid from the first group at one of the two ends of the sequence motif is thus considered to be positioned alone, even if the preceding (N-terminus) or subsequent (C-terminus) amino acid residue outside of the sequence motif is by chance also an arginine, histidine or lysine residue.

"Pairwise together with a further amino acid selected from the first group" means that within the sequence motif an amino acid selected from the first group is directly adjacent to another amino acid selected from the first group. This two amino acids form thereby a pair of amino acids selected from the first group. Said pair in turn is flanked C-terminally and N-terminally by amino acids from the second or, as the case may be, from the third group (e.g., LKRE (SEQ ID NO:86), N-KRE (at N-terminus of motif), LKR-C (at C-terminus of motif)). Potential further amino acids within the peptide component of the inventive polypeptide, but outside of the sequence motif, are again not taken into account for this positional determination.

"In a block with 2 further amino acids selected from the first group" means that three amino acids selected from the first group are directly adjacent to each other. Said block (or triplet) is flanked C-terminally and N-terminally by amino acids from the second or, as the case may be, from the third group (e.g., LKRKE (SEQ ID NO:87), N-KRKE (at N-terminus of motif; SEQ ID NO:88), LKRK-C (at C-terminus of motif; SEQ ID NO:89)). Potential further amino acids within the peptide component of the inventive polypeptide, but outside of the sequence motif, are again not taken into account for this positional determination. For amino acids arranged in such manner (triplet; block with 3 amino acids of the first group) an additional positional requirement must be met, namely that none of the amino acids at positions −12, −11, −8, −5, −4, +6, +7, +10, +13, and +14 relative to the first amino acid of the 3 amino acid block is—provided the respective position may be found in said sequence motif—an amino acid selected from said first group. Negative values indicate positions N-terminal of the first amino acid of the triplet; positive values refer to positions C-terminal of the first amino acid of the triplet. Basis for the positional calculation is the first (N-terminal) amino acid of the triplet (e.g. the amino acid directly N-terminal of the triplet would be −1, the amino acid directly C-terminal of the triplet would be +3). This limitation thus precludes a sequence like RRRGLRH (SEQ ID NO:90), because position +6 (H) is an amino acid of the first group. Whether the respective positions (−12, −11, −8, −5, −4, +6, +7, +10, +13, and +14) are present in the sequence motif or not will be dependent on the position of the triplet within the sequence motif and the length of the sequence motif. For example, if the triplet would be situated at the N-terminus of the sequence motif, then all negative values are obsolete (i.e. need not be taken into account). The same applies for the positive values, if the triplet is situated at the C-terminus of the sequence motif. However, in preferred embodiments, the sequence motif does not comprise such triplet block of amino acids of the first group at all, i.e. does not comprise a block consisting of 3 amino acids selected from the first group.

It is understood that the positional requirements alone, pairwise together with a further amino acid selected from the first group, and in a block with 2 further amino acids selected from the first group are not overlapping and the terms are mutual exclusive (e.g. a triplet is not a case of "alone" and/or "pairwise together", etc.).

A further positional requirement for the amino acids selected from the first group is, that the sequence motif must comprise at least 2 pairs of amino acids selected from the first group. However, it is preferred that not all amino acids selected from the first group are arranged pairwise in the sequence motif.

The sequence motif of the inventive polypeptide does not comprise blocks of 4 (quartet) or more amino acids (quintet, sextet, etc.) selected from the first group (i.e. an amino acid of the first group does not occur in a block with 3 or more amino acids selected from the first group). The sequence motif may thus for example not comprise sequences such as "KRKK" (SEQ ID NO:91) or "RRRR" (SEQ ID NO:92).

As amino acids of the first group make up only 40% to 60% of the sequence motif, the remaining amino acids need to be selected from other amino acid residues. As set out above, the sequence motif comprises also at least 40% and at most 60% amino acids selected from a second group of amino acids. Said second group consists of the amino acid residues alanine, glycine, isoleucine, leucine, phenylalanine, serine, threonine, tryptophan, tyrosine and valine. As before for the first group of amino acids, each of the amino acids of the second group is likewise in principle selected independently, i.e. each amino acid is selected independent from any previous or subsequent selections from said second group.

However, for the second group there are preferably some restrictions to this general principle of independent selection. The first restriction preferably applies, if the sum of amino acids selected from the first group and selected from the second group yields 100% of the amino acids of the sequence motif (i.e. there are no amino acids from the third group in the sequence motif). In such scenario at least three different amino acids are preferably selected from the second group. In such scenario the amino acids of the second group may for example preferably not be restricted to valine and tryptophan residues only.

A further preferred (positional) restriction is that the sequence motif may not comprise the triplet sequence AFV (alanine, phenylalanine, valine), if the sequence motif contains at least two single, non-adjacent phenylalanine residues and at least one of these phenylalanine residues is (N-terminally) directly preceded by a lysine residue (i.e. KF). Nonadjacent phenylalanine residues are phenylalanine residues which do not occur in a row in the sequence, but which are separated by one or more other amino acids. Single phenylalanine residues means that they are not part of a pair of phenylalanine residues or of a block of several phenylalanine residues but are positioned alone in the sequence motif.

The next preferred restriction is, that the sequence motif does not comprise the sequence AALTH (SEQ ID NO: 85, i.e., alanine, alanine, lysine, threonine, histidine), if the sequence motif contains at least three single, non-adjacent histidine residues. Nonadjacent histidine residues are histidine residues which do not occur in a row, but which are separated by one or more other amino acids. Single histidine residues means that they are not part of a pair of histidine residues or of a block of several histidine residues but are positioned alone in the sequence motif.

In a preferred embodiment, less than 5 isoleucine residues (e.g. 4, 3, 2, 1 or 0) are selected from said second group.

It is possible, that the sequence motif of the peptide component of the polypeptide of the invention is not exclusively composed of amino acids selected from the first and second group (i.e. they represent together less than 100%). In such scenario, the remaining amino acids of said sequence motif are selected from a third group of amino acids, said group consisting of asparagine, aspartic acid, glutamine, glutamic acid, methionine, and cysteine. As before for the first and second group of amino acids, each of the amino acids of the third group is likewise in principle selected independently, i.e. each amino acid is selected independent from any previous or subsequent selections from said third group. However, as before for the second group, there are some preferred restrictions to the selection of an amino acid from said third group: glutamine may be selected only once and a selection of glutamine and glutamic acid in parallel is also not allowed, i.e. if glutamine is present in the sequence motif, then no glutamic acid may be present and vice versa). Preferably, the amino acids selected from the third group are limited to asparagine, aspartic acid, glutamine and glutamic acid, i.e. the selected third group amino acids do not comprise methionine or cysteine residues.

In preferred embodiments, the sequence motif comprises only a single, or even more preferred no amino acid residue at all from the third group.

In preferred embodiments of the present invention, the arrangement of the selected amino acids in the sequence motif complies with the requirements set out in one of the possible sequence motif alternatives depicted in FIG. 1. FIG. 1 specifies that at specific positions for a given 16mer, 17mer, 18mer, 19mer or 20mer no amino acids selected from the first group may be present. At these positions only amino acids selected from the second and/or the third group (if any) may be present. Preferably, amino acids of the second group are present at said positions. Amino acids of the first group may only be present at any of the remaining positions of the sequence motif. This does not imply that at these remaining positions only amino acids of the first group may be found. Amino acids of the second and optionally third group may also be found at these remaining positions, provided the overall percentage requirements for the first and second group are still met.

Preferably, the sequence motif of the peptide component is of helical structure.

The preferred sequence motif of the peptide component does not comprise any other amino acid residues than those defined to be in the first, second or third group. In particular, the preferred sequence motif of the peptide component does not comprise any proline residue, and if the third group is limited to asparagine, aspartic acid, glutamine and glutamic acid, no methionine and cysteine as well.

However, a proline residue may very well be present elsewhere in the peptide component (or inventive polypeptide). It is for example preferred, if a proline residue is located within 1 to 10, preferably 1 to 5 amino acid residues N-terminal or C-terminal of the sequence motif, with the latter being preferred. It is furthermore preferred if such proline residue is found between the sequence of the endolysin and the sequence motif Preferably, the sequence motif is N-terminal of the sequence of the endolysin and the proline residue is positioned somewhere in between, usually close to the sequence motif.

Examples for peptide components exhibiting the above discussed preferred sequence motif are peptides comprising the sequence of SEQ ID NO:37, SEQ ID NO:93, SEQ ID NO:94, SEQ ID NO:95, SEQ ID NO:96, SEQ ID NO:97, SEQ ID NO:98, SEQ ID NO:99, SEQ ID NO:100, SEQ ID NO:101, SEQ ID NO:102, SEQ ID NO:103, SEQ ID NO:104, SEQ ID NO:105 SEQ ID NO:106, SEQ ID NO:107, SEQ ID NO:108, SEQ ID NO:109 and SEQ ID NO:110. A particularly preferred peptide component exhibiting the above mentioned sequence motif is SEQ ID NO:106.

The peptide (component) of the inventive polypeptide consists preferably of at least 5, more preferably at least of 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 or at least 100 amino acid residues. Especially preferred are those peptides consisting of about 5 to about 100 amino acid residues, about 5 to about 50 or about 5 to about 30 amino acid residues. More preferred are peptide stretches consisting of about 6 to about 42 amino acid residues, about 6 to about 39 amino acid residues, about 6 to about 38 amino acid residues, about 6 to about 31 amino acid residues, about 6 to about 25 amino acid residues, about 6 to about 24 amino acid residues, about 6 to about 22 amino acid residues, about 6 to about 21 amino acid residues, about 6 to about 20 amino acid residues, about 6 to about 19 amino acid residues, about 6 to about 16 amino acid residues, about 6 to about 14 amino acid residues, about 6 to about 12 amino acid residues, about 6 to about 10 amino acid residues or about 6 to about 9 amino acid residues.

In a preferred embodiment the inventive polypeptide comprises at least one amino acid sequence selected from the group consisting of KRK and SEQ ID NOs: 11-110.

The peptide component of the polypeptide according to the present invention may be linked to the endolysin by intervening additional amino acid residues e.g. due to cloning reasons. Alternatively, the peptide component may be directly linked to the endolysin sequence without any intervening linker sequences.

Preferably, said intervening additional amino acid residues may not be recognized and/or cleaved by proteases. Preferably said additional amino acid sequences are linked to each other and/or to the enzyme by at least 1, 2, 3, 4, 5, 6, 7, 8, 9 or 10 additional intervening amino acid residues.

In a preferred embodiment the peptide is linked to the rest of the inventive polypeptide, preferably at the N- or C-terminus of the polypeptide according to the present invention, by the additional intervening amino acid residues glycine, serine and serine (Gly-Ser-Ser), glycine, alanine, glycine and alanine (Gly-Ala-Gly-Ala; SEQ ID NO:111), glycine, alanine, glycine, alanine, glycine, alanine, glycine and alanine (Gly-Ala-Gly-Ala-Gly-Ala-Gly-Ala; SEQ ID NO:112) or glycine, alanine, glycine, alanine, glycine, alanine, glycine, alanine, glycine, alanine, glycine and alanine (Gly-Ala-Gly-Ala-Gly-Ala-Gly-Ala-Gly-Ala-Gly-Ala; SEQ ID NO:113).

Preferably, the peptide component is situated N-terminal of the endolysin within the inventive polypeptide. In such scenario (in particular for the third aspect of the polypeptide of the present invention, but not limited thereto) it is particularly preferred that the endolysin constitutes the most C-terminal component of the polypeptide, i.e. there are no further functional elements C-terminal of the endolysin sequence. Preferably, there are 10 or less, more preferably 5 or less, more preferably 4 or less, more preferably 3 or less, more preferably 2 or less, more preferably only 1 and most preferably no amino acids C-terminal of the endolysin sequence in an inventive polypeptide.

Examples of polypeptides of the present invention are polypeptides comprising for instance as an endolysin SEQ ID NO:7 or SEQ ID NO:8 (or a sequence sharing at least 80% sequence identity therewith) and further comprising as peptide component SEQ ID NO:37 or SEQ ID NO:106. Particularly preferred polypeptides according to the present invention are polypeptides comprising SEQ ID NO:114 or SEQ ID NO:115 and polypeptides sharing at least 80% sequence identity, preferably at least 85% sequence identity, more preferably at least 90% sequence identity, more preferably at least 95% sequence identity, more preferably at least 96% sequence identity, more preferably at least 97% sequence identity, more preferably at least 98% sequence identity, more preferably at least 99% sequence identity with SEQ ID NO:114 and/or SEQ ID NO:115.

Other examples of polypeptides according to the present invention are polypeptides comprising a peptide component selected from the group consisting of SEQ ID NO: 70, SEQ ID NO: 81, SEQ ID NO:106, SEQ ID NO: 107, SEQ ID NO: 108, SEQ ID NO: 109 or SEQ ID NO: 110. Examples for such inventive polypeptides are provided as SEQ ID NO:116, SEQ ID NO:117, SEQ ID NO:118, SEQ ID NO:119, SEQ ID NO:120, and SEQ ID NO:121, as well as polypeptides sharing at least 80% sequence identity, preferably at least 85% sequence identity, more preferably at least 90% sequence identity, more preferably at least 95% sequence identity, more preferably at least 96% sequence identity, more preferably at least 97% sequence identity, more preferably at least 98% sequence identity, more preferably at least 99% sequence identity with any of these sequences.

SEQ ID NO:114, SEQ ID NO:115, SEQ ID NO:117, SEQ ID NO:118, SEQ ID NO:119 and SEQ ID NO:121 exhibit an alanine residue at the N-terminus (e.g. instead of a methionine residue). Said alanine residue is not critical and merely remained after proteolytic removal of a His-Tag at the N-terminus. In the case of SEQ ID NO:120 proteolytic removal of the His-Tag at the N-terminus left no additional amino acid, i.e. the polypeptide directly starts with the peptide according to SEQ ID NO:109.

Aside of the endolysin and peptide, as defined herein, the inventive polypeptide may of course also comprise other amino acid sequence elements, e.g. one or more tags, e.g. a His-tag, Strep-tag, Avi-tag, Myc-tag, Gst-tag, JS-tag, cystein-tag, FLAG-tag or other tags known in the art, thioredoxin, maltose binding proteins (MBP) etc.

In this context, the inventive polypeptide may additional comprise a tag e.g. for purification. Preferred is a His6-tag (SEQ ID NO: 122), preferably at the C-terminus and/or the N-terminus of the polypeptide according to the present invention. Said tag can be linked to the polypeptide by additional amino acid residues e.g. due to cloning reasons. Preferably said tag can be linked to the protein by at least 1, 2, 3, 4, 5, 6, 7, 8, 9 or 10 additional amino acid residues. Preferably said additional amino acid residues may be recognized and/or cleaved by proteases. In a preferred embodiment the inventive polypeptide comprises a His6-tag at its N-terminus.

In a fourth aspect the present invention relates to a polypeptide comprising the sequence of a peptide selected from the group consisting of SEQ ID NO: 81, SEQ ID NO:107, SEQ ID NO:108, SEQ ID NO:109 and SEQ ID NO: 110, and optionally further comprising the sequence of a muralytic enzyme. The muralytic enzyme of the polypeptide according to the fourth aspect of the invention may be any muralytic enzyme (in particular peptidoglycan hydrolase) capable of degrading bacterial peptidoglycan. Such muralytic enzyme may be in terms of enzymatic activity for example an endopeptidase, N-acetyl-muramoyl-L-alanineamidase (amidase), N-acetyl-muramidase, N-acetyl-glucosaminidase or lytic transglycosylase and is thus suitable for degrading the peptidoglycan of bacterial cell walls. Preferably, the muralytic enzyme degrades the peptidoglycan of Gram-negative bacteria, such as E. coli or P. aeruginosa. The peptidoglycan structure of a bacterial cell wall is overall largely conserved with minor modifications (Schleifer & Kandler 1972). Bacterial species have interpeptide bridges composed of different amino acids or may even lack an interpeptide bridge. In peptidoglycan structures lacking an interpeptide bridge a Diaminopimelic acid (DAP) or meso-Diaminopimelic acid (mDAP; an amino acid, representing an epsilon-carboxy derivative of lysine being a typical component of peptidoglycan) (Diaminopimelic acid is residue replaces the amino acid L-Lys and directly cross-links to the terminal amino acid D-Ala of the opposite peptide chain. Thus, there are limited types of chemical bonds available that can be cleaved by muralytic enzymes (e.g. hydrolyzed by peptidoglycan hydrolases). The muralytic enzymes exhibit at least one enzyme domain having an enzymatic activity as listed above. In addition the muralytic enzymes contain in some cases at least one domain suitable for binding to the peptidoglycan and supporting the enzymatic activity of the muralytic enzyme. The binding domains are typically called cell-wall binding domains (CBD). Examples of muralytic enzymes are vertebrate lysozymes (such as hen egg white lysozyme and human lysozyme), endolysins (e.g. KZ144 endolysin or Lys394 endolysin), Virion-associated peptidoglycan hydrolases (VAPGH), bacteriocins (e.g. lysostaphin) and autolysins. Most preferably, the muralytic enzyme is an endolysin. Particularly preferred endolysin sequences are those set out above for the first to third aspect of the invention, e.g. SEQ ID NO:4, SEQ ID NO:5, SEQ ID NO:6, SEQ ID NO:7, SEQ ID NO:8 and SEQ ID NO:9, or a sequence having at least 80% sequence identity, preferably at least 85% sequence identity, more preferably at least 90% sequence identity, more preferably at least 95% sequence identity, more preferably at least 96% sequence identity, more preferably at least 97% sequence identity, more preferably at least 98% sequence identity, more preferably at least 99% sequence identity with SEQ ID NO:4, SEQ ID NO:5, SEQ ID NO:6, SEQ ID NO:7, SEQ ID NO:8 and/or SEQ ID NO:9. In general: what has been set out above for an inventive polypeptide (according to the first to third aspect of the invention) applies (to the extent applicable) likewise to an inventive polypeptide according to the fourth aspect of the invention.

An inventive polypeptide comprises, or may comprise, a Gram negative endolysin. A polypeptide of the invention will therefore preferably be capable of degrading the peptidoglycan of at least on Gram-negative bacterium, usually the host species of the respective parental phage. Preferably, a polypeptide of the present invention will be capable of degrading the peptidoglycan of E. coli bacteria and/or P. aeruginosa bacteria. Most preferably, a polypeptide of the present invention degrades the peptidoglycan of E. coli strain RKI 06-08410 (obtained from Robert Koch-Institut, Berlin, Germany).

Peptidoglycan degrading activity on Gram-negative bacteria can be measured by assays well known in the art, e.g. by muralytic assays in which the outer membrane of Gram-negative bacteria is permeabilized or removed (e.g. with chloroform) to allow the putative enzyme access to the peptidoglycan layer. If the enzyme is active, degradation of the peptidoglycan layer will lead to a drop of turbidity, which can be measured photometrically (see for example Briers et al., J. Biochem. Biophys Methods 70: 531-533, (2007) or Schmelcher et al., Bacteriophage endolysins as novel antimicrobials. Schmelcher M, Donovan D M, Loessner M J. Future Microbiol. 2012 October; 7(10):1147-7) (both references incorporated herein by reference).

A polypeptide of the present invention will typically not only exhibit the activity of a peptidoglycan degrading enzyme, i.e. is capable of degrading Gram-negative bacterial peptidoglycan. Preferably, a polypeptide of the present invention will be capable of degrading the peptidoglycan of Gram-negative bacteria (e.g. E. coli bacteria and/or P. aeruginosa bacteria) in absence of EDTA (or any other auxiliary substance increasing the permeability of the outer membrane). More preferably, the inventive polypeptide exhibits a minimal inhibitory concentration (MIC) of 40 µg/ml or less in absence of other outer membrane permeabilizers), preferably of 30 µg/ml or less, even more preferably of 25 µg/ml or less even more preferably of 20 µg/ml or less, most preferably of 15 µg/ml or less. Most preferably, the polypeptide degrades the peptidoglycan of E. coli strain RKI 06-08410 with a minimal inhibitory concentration (MIC) of 40 µg/ml or less in absence of other outer membrane permeabilizers), preferably of 30 µg/ml or less, more preferably of 25 µg/ml or less, even more preferably of 20 µg/ml or less, most preferably of 15 µg/ml or less. A corresponding suitable test is set forth in Example 1. For P. aeruginosa, a suitable test is set forth in Example 2 and the respective test strain is preferably PAO1 (Pirnay et al., Environmental Microbiology, 2002, p. 898-911).

A polypeptide according to the present invention can be produced by standard means known in the art, e.g. by recombinant expression of nucleic acids encoding the respective polypeptide in appropriate host cells. If the inventive polypeptide comprises for example additionally amino acid sequence stretches or tags etc., such fusion proteins may be produced by linking the required individual nucleic acid sequences using standard cloning techniques as described e.g. by Sambrook et al. 2001, Molecular Cloning: A Laboratory Manual. Such a polypeptide may be produced likewise with methods known in the art, e.g., in recombinant DNA expression systems.

The present invention does also relate to nucleic acids encoding one or more inventive polypeptides of the present invention. The inventive nucleic acid may take all forms conceivable for a nucleic acid. In particular the nucleic acids according to the present invention may be RNA, DNA or hybrids thereof. They may be single-stranded or double-stranded. The may have the size of small transcripts or of entire genomes, such as a bacteriophage genome. As used herein, a nucleic acid encoding one or more inventive polypeptides of the present invention may be a nucleic acid reflecting the sense strand. Likewise, the antisense strand is also encompassed. The nucleic acid may encompass a heterologous promotor for expression of the inventive polypeptide.

In a further aspect the present invention relates to a vector comprising a nucleic acid according to the present invention. Such vector may for example be an expression vector allowing for expression of an inventive polypeptide. Said expression vector may be constitutive or inducible. The vector may also be a cloning vector comprising the nucleic acid sequence of the current invention for cloning purposes.

The present invention does also relate to a bacteriophage comprising an inventive nucleic acid, in particular comprising an inventive nucleic acid encoding a fusion protein according to the present invention.

The present invention does also relate to (isolated) host cells comprising a polypeptide, nucleic acid, vector, or bacteriophage according to the present invention. The host cells may be selected in particular from the group consisting of bacterial cells and yeast cells. Where appropriate, other suitable host cells may be immortalized cell lines, e.g. of mammalian (in particular human) origin.

In a further aspect the present invention relates to a composition comprising a polypeptide according to the present invention, a nucleic acid according to the present invention, a vector according to the present invention, a bacteriophage according to the present invention and/or a host cell according to the present invention. A composition according to the present invention may be a pharmaceutical composition comprising a pharmaceutical acceptable diluent, excipient or carrier. Particularly preferred are compositions comprising a polypeptide according to the present invention but are free of EDTA. Preferably, the composition of the invention is free of any other outer membrane permeabilizing substance.

In an even further aspect the composition according to the present invention is a cosmetic composition. Several bacterial species can cause irritations on environmentally exposed surfaces of the patient's body such as the skin. In order to prevent such irritations or in order to eliminate minor manifestations of said bacterial pathogens, special cosmetic preparations may be employed, which comprise sufficient amounts of the inventive polypeptide, nucleic acid, vector, host cell and/or composition in order to achieve a comedolytic effect. Preferably, the inventive polypeptide, nucleic acid, vector, bacteriophage, host cell or composition is used in this context without any other outer membrane permeabilizing substance.

In a further aspect the present invention relates to a kit comprising a polypeptide according to the present invention, a nucleic acid according to the present invention, a vector according to the present invention, a bacteriophage according to the present invention and/or a host cell according to the present invention, and at least one further antimicrobial agent, such as a further polypeptide according to the present invention, an antibiotic or an antimicrobial peptide.

In a further aspect the present invention relates to a polypeptide according to the present invention, a nucleic acid according to the present invention, a vector according to the present invention, a bacteriophage according to the present invention, a host cell according to the present invention, and/or a composition according to the present invention for use in a method of treatment of the human or animal body by surgery or therapy or in diagnostic methods practiced on the human or animal body. In such scenarios the antibacterial activity of polypeptide of the present invention can be exploited.

Such method typically comprises administering to a subject an effective amount of an inventive polypeptide, nucleic acid, vector, bacteriophage, host cell or a composition. Preferably the polypeptide, nucleic acid, vector, bacteriophage, host cell or a composition is administered without addition of further outer membrane permeabilizing substances such as EDTA. The subject may for example be a human or an animal, with human subjects being more preferred. In particular, the inventive polypeptide, the inventive nucleic acid, the inventive vector, the inventive bacteriophage, the inventive host cell, and/or the inventive composition may be used in methods for the treatment or prevention of bacterial infections, such Gram-negative bacterial infections. Without being limited thereto, the method of treatment may comprise the treatment and/or prevention of infections of the skin, of soft tissues, the respiratory system, the lung, the digestive tract, the eye, the ear, the teeth, the nasopharynx, the mouth, the bones, the vagina, of wounds of bacteraemia and/or endocarditis.

The dosage and route of administration used in a method of treatment (or prophylaxis) according to the present invention depends on the specific disease/site of infection to be treated. The route of administration may be for example oral, topical, nasopharyngeal, parenteral, intravenous, rectal or any other route of administration.

For application of an inventive polypeptide, nucleic acid, vector, bacteriophage, host cell or composition to a site of infection (or site endangered to be infected) a formulation may be used that protects the active compounds from environmental influences such as proteases, oxidation, immune response etc., until it reaches the site of infection. Therefore, the formulation may be capsule, dragee, pill, suppository, injectable solution or any other medical reasonable galenic formulation. Preferably, the galenic formulation may comprise suitable carriers, stabilizers, flavourings, buffers or other suitable reagents. For example, for topical application the formulation may be a lotion or plaster, for nasopharyngeal application the formulation may be saline solution to be applied via a spray to the nose. Preferably, the formulation does not comprise any other outer membrane permeabilizing substance (other than the inventive polypeptide).

Preferably, an inventive polypeptide, nucleic acid, vector, bacteriophage, host cell or composition is used in combination with other conventional antibacterial agents, such as antibiotics, lantibiotics, bacteriocins or endolysins, etc. The administration of the conventional antibacterial agent can occur prior to, concurrent with or subsequent to administration of the inventive polypeptide (e.g. fusion protein), nucleic acid, vector, bacteriophage, host cell or composition.

In a further aspect the present invention relates to the inventive polypeptide, nucleic acid, vector, bacteriophage, host cell or composition for use as diagnostic means in medical diagnostics, food diagnostics, feed diagnostics, or environmental diagnostics, in particular as a diagnostic means for the diagnostic of bacterial infection, in particular those caused by Gram-negative bacteria. In this respect the inventive polypeptide, nucleic acid, vector, host cell or composition may be used as a tool to specifically degrade the peptidoglycan of Gram-negative pathogenic bacteria. Specific cell degradation is needed as an initial step for subsequent specific detection of bacteria using nucleic acid based methods like PCR, nucleic acid hybridization or NASBA (Nucleic Acid Sequence Based Amplification), immunological methods like IMS, immunofluorescence or ELISA techniques, or other methods relying on the cellular content of the bacterial cells like enzymatic assays using proteins specific for distinct bacterial groups or species (e.g. β-galactosidase for enterobacteria, coagulase for coagulase positive strains). Preferably, the inventive polypeptide, nucleic acid, vector, bacteriophage, host cell or composition is used in this context without any other outer membrane permeabilizing substance.

In a further aspect the present invention relates to the use of the inventive polypeptide, the inventive nucleic acid, the inventive vector, the inventive bacteriophage, the inventive host cell, and/or the inventive composition, as an antimicrobial in food, in feed, or in cosmetics, or as a (e.g., non-therapeutic) disinfecting agent. An inventive polypeptide can be used for the treatment or prevention of Gram-negative bacterial contamination of foodstuff, of food processing equipment, of food processing plants, of (inanimate)

surfaces coming into contact with foodstuff (such as shelves and food deposit areas), of feedstuff, of feed processing equipment, of feed processing plants, of (inanimate) surfaces coming into contact with feedstuff (such as shelves and feed deposit areas), of medical devices, or of (inanimate) surfaces in hospitals, doctor's offices and other medical facilities. Preferably, the inventive polypeptide, nucleic acid, vector, bacteriophage, host cell or composition is used in this context without any other outer membrane permeabilizing substance.

FIGURE

In the following a brief description of the appended FIGURE will be given. The FIGURE is intended to illustrate an aspect of the present invention in more detail. However, it is not intended to limit the subject matter of the invention to such subject-matter only.

FIG. 1: illustrates positional requirements of preferred sequence motifs of selected peptide components of the inventive polypeptide. The table indicates for sequence motifs of 16 (white) to 20 (dark grey) amino acids in length positions at which no amino acid selected from the first group may be present (respective positions are labelled with "X"). At said positions (i.e. those labelled with "X"), only amino acids selected from the second, or as the case may be, from the third group may be present. More preferably, only amino acids selected from the second group are present at said positions. Amino acids selected from the first group of the sequence motif may only be present at positions which are not labelled with an "X". However, at said non-labelled positions, amino acids of the second, or as the case may be, third group may also be present. Altogether 18 alternatives, each for a length of 16, 17, 18, 19 or 20 amino acids are provided. The table also clearly specifies the position where potentially a triplet amino acid of the first group may be present (three positions in a row without "X"). For alternative 1 this would be positions 8 to 10. As required for the preferred sequence motif of the peptide component polypeptide of the present invention, the amino acids at positions −5 (i.e. position #3), −4 (i.e. position #4), +6 (i.e. position #14), +7 (i.e. position #15), and +10 (i.e. position #18) relative to the first amino acid of the 3 amino acid block (i.e. position #8) are not to be selected from the first group. The relative positions 12, −11, −8, +13, and +14 cannot be found in the first alternative and are thus not taken into account.

EXAMPLES

In the following a specific example illustrating embodiments and aspects of the invention is presented. However, the present invention shall not to be limited in scope by the specific embodiments described herein. Indeed, various modifications of the invention in addition to those described herein will become readily apparent to those skilled in the art from the foregoing description and the example below. All such modifications fall within the scope of the appended claims.

Example 1: Minimal Inhibitory Concentration of Several Antibacterial Polypeptides Against *E. coli* in Presence and Absence of EDTA The antibacterial activity of the following fusion proteins on *E. coli* in presence and absence of EDTA was assessed:

SEQ ID NO:123, a fusion of Cecropin A. (*A aegyptii*) peptide (SEQ ID NO: 43) with the endolysin of *Vibrio* phage VvAW1 (YP_007518361.1)

SEQ ID NO:124, a fusion of Cecropin A. (*A aegyptii*) peptide with a mutated cell wall binding domain of the modular KZ144 endolysin and Lys68 endolysin SEQ ID NO:125, a fusion of a modified peptide (SEQ ID NO:105) complying with the preferred sequence motif of the peptide component and an endolysin of *Pseudomonas* phage vB_PsyM_KIL1 (see YP_009276009.1)

SEQ ID NO:114, a fusion of SMAP-29 peptide (SEQ ID NO:37) and the endolysin of *Citrobacter koseri* phage CkP1, with the additional technical modification of a C54S mutation to reduce aggregation (SEQ ID NO:7), SEQ ID NO:115, a fusion of a peptide comprising the preferred sequence motif for the peptide component (SEQ ID NO:106) and the endolysin of Enterobacteria phage CC31, with the additional technical modification of a C54S mutation to reduce aggregation (SEQ ID NO:8)

SEQ ID NO:116, a fusion of the peptide according to SEQ ID NO: 107 and the endolysin of *Citrobacter koseri* phage CkP1, with the additional technical modification of a C54S mutation to reduce aggregation (SEQ ID NO:7), SEQ ID NO:117, a fusion of a peptide comprising a preferred sequence according to SEQ ID NO:108 and the endolysin of Enterobacteria phage CC31, with again the additional technical modification of a C54S mutation to reduce aggregation (SEQ ID NO:8), SEQ ID NO:119, a fusion of a peptide comprising a preferred sequence according to SEQ ID NO:81 and the endolysin of *Serratia* phage CHI14, with again the additional technical modification of a C54S mutation to reduce aggregation (SEQ ID NO:9), and SEQ ID NO:120, a fusion of a peptide comprising a preferred sequence according to SEQ ID NO:109 and the endolysin of *Citrobacter koseri* phage CkP1, with the additional technical modification of a C54S mutation to reduce aggregation (SEQ ID NO:7).

The endolysin components of the polypeptide of SEQ ID NO:114 and the polypeptide of SEQ ID NO:115 (see SEQ ID NO:7 and SEQ ID NO:8) share a significant level of sequence identity (80%).

Likewise, the endolysin components of the polypeptide of SEQ ID NO:114 and the polypeptide of SEQ ID NO:119, (see SEQ ID NO:7 and SEQ ID NO:9) share a significant level of sequence identity (80%).

*E. coli* bacteria (*E. coli* strain RKI 06-08410; obtained from Robert Koch-Institut, Berlin, Germany) were grown in (Luria-Bertani) medium and diluted 1:10 in Mueller-Hinton medium. At an optical density $OD_{600}$ of about 0.6 bacteria were diluted in the same medium 1:10 followed by a 1:500 dilution. Protein buffer (20 mM HEPES, 150 mM NaCl, pH 7.4) and proteins were pipetted into a 96 well plate using different concentrations of proteins in an end volume of 20 µl with or without a final concentration of 500 µM EDTA. 180 µl of bacterial cell suspension or medium (Mueller-Hinton) as control were given to the 96 well plate and mixed. The plate was incubated for 18-22 hours at 37° C. and the bacterial growth was determined measuring the OD600 values of the wells. The minimal inhibitory concentration (MIC), which is the protein concentration in the well which showed the same OD600 value as the no-bacteria control, was determined.

The results in form of minimal inhibitory concentration (MIC in µg/ml) are shown in table 3 below.

TABLE 3

Antibacterial activity in presence and absence of EDTA

| SEQ ID NO | MIC (µg/ml) with EDTA | MIC (µg/ml) w/o EDTA |
|---|---|---|
| SEQ ID NO: 123 | <5 | 25 |
| SEQ ID NO: 124 | ≤5 | >50 |
| SEQ ID NO: 125 | <5 | >50 |
| SEQ ID NO: 114 | ≤5 | 10 |
| SEQ ID NO: 115 | ≤5 | 10 |
| SEQ ID NO: 116 | <5 | 15 |
| SEQ ID NO: 117 | ≤5 | 10 |
| SEQ ID NO: 119 | ≤5 | 7.5 |
| SEQ ID NO: 120 | ≤3.3 | 16.7 |

"≤" (e.g. ≤5, ≤3.3 or the like) means, that antibacterial activity was observed already at the first concentration tested (e.g., 5 µg/ml and 3.3 µg/ml, respectively). The MIC is thus at least the first tested concentration (e.g., 5 µg/ml and 3.3 µg/ml, respectively) and possibly lower. >50 means, that no antibacterial activity could be observed up to a concentration of 50 µg/ml.

All polypeptides tested showed good antibacterial activity against *E. coli* in presence of the outer membrane permeabilizer EDTA. However, in absence of EDTA, the antibacterial activity for three conventional fusion proteins dropped significantly. In contrast, the polypeptides according to the present invention retained a significant level of antimicrobial activity even in absence of EDTA.

Example 2: Minimal Inhibitory Concentration of Several Antibacterial Polypeptides Against *P. aeruginosa* in Presence and Absence of EDTA The antibacterial activity on *P. aeruginosa* bacteria in presence and absence of EDTA was also assessed. The following polypeptides were used:
  SEQ ID NO:123, a fusion of Cecropin A. (*A aegyptii*) peptide (SEQ ID NO: 43) with the endolysin of *Vibrio* phage VvAW1 (YP_007518361.1)
  SEQ ID NO:124, a fusion of Cecropin A. (*A aegyptii*) peptide with a mutated cell wall binding domain of the modular KZ144 endolysin and Lys68 endolysin
  SEQ ID NO:125, a fusion of a modified peptide (SEQ ID NO:105) complying with the preferred sequence motif of the peptide component and an endolysin of *Pseudomonas* phage vB_PsyM_KIL1 (see YP_009276009.1)
  SEQ ID NO:114, a fusion of SMAP-29 peptide (SEQ ID NO:37) and the endolysin of *Citrobacter koseri* phage CkP1, with the additional technical modification of a C54S mutation to reduce aggregation (SEQ ID NO:7), and
  SEQ ID NO:115, a fusion of a peptide comprising the preferred sequence motif for the peptide component (SEQ ID NO:106) and the endolysin of Enterobacteria phage CC31, with the additional technical modification of a C54S mutation to reduce aggregation (SEQ ID NO:8)
  SEQ ID NO:118, a fusion of a peptide comprising a preferred sequence according to SEQ ID NO: SEQ ID NO:106 and the endolysin of *Serratia* phage CHI14, with again the additional technical modification of a C54S mutation to reduce aggregation (SEQ ID NO:9),
  SEQ ID NO:119, a fusion of a peptide comprising a preferred sequence according to SEQ ID NO:81 and the endolysin of *Serratia* phage CHI14, with again the additional technical modification of a C54S mutation to reduce aggregation (SEQ ID NO:9),
  SEQ ID NO:120, a fusion of a peptide comprising a preferred sequence according to SEQ ID NO:109 and the endolysin of *Citrobacter koseri* phage CkP1, with the additional technical modification of a C54S mutation to reduce aggregation (SEQ ID NO:7),
  SEQ ID NO:121, a fusion of a peptide comprising a preferred sequence according to SEQ ID NO:110 and the endolysin of *Citrobacter koseri* phage CkP1, with the additional technical modification of a C54S mutation to reduce aggregation (SEQ ID NO:7), and Bacteria (*P. aeruginosa* PAO1) were grown in (Luria-Bertani) medium and diluted 1:10 in Mueller-Hinton medium. At an optical density $OD_{600}$ of about 0.6 bacteria were diluted in the same medium 1:10 followed by a 1:500 dilution. Protein buffer (20 mM HEPES, 150 mM NaCl, pH 7.4) and proteins were pipetted into a 96 well plate using different concentrations of proteins in an end volume of 20 µl with or without a final concentration of 500 µM EDTA. 180 µl of bacterial cell suspension or medium (Mueller-Hinton) as control were given to the 96 well plate and mixed. The plate was incubated for 18-22 hours at 37° C. and the bacterial growth was determined measuring the OD600 values of the wells. The MIC which is the protein concentration in the well which showed the same OD600 value as the no-bacteria control was determined.

The results in form of minimal inhibitory concentration (MIC in µg/ml) are shown in table 4 below.

TABLE 4

Antibacterial activity in presence and absence of EDTA

| SEQ ID NO | MIC (µg/ml) with EDTA | MIC (µg/ml) w/o EDTA |
|---|---|---|
| SEQ ID NO: 123 | ≤5 | >50 |
| SEQ ID NO: 124 | ≤5 | >50 |
| SEQ ID NO: 125 | 10 | >50 |
| SEQ ID NO: 114 | ≤5 | 5 |
| SEQ ID NO: 115 | ≤5 | 10 |
| SEQ ID NO: 118 | ≤4.5 | 6.8 |
| SEQ ID NO: 119 | ≤5 | 7.5 |
| SEQ ID NO: 120 | ≤3.3 | 8.3 |
| SEQ ID NO: 121 | ≤5 | 15 |

"≤" (e.g. ≤5, ≤3.3 or the like) means, that antibacterial activity was observed already at the first concentration tested (e.g., 5 µg/ml and 3.3 µg/ml, respectively). The MIC is thus at least the first tested concentration (e.g. 5 µg/ml and 3.3

μg/ml, respectively) and possibly lower. >50 means, that no antibacterial activity could be observed up to a concentration of 50 μg/ml.

All polypeptides tested showed good antibacterial activity against *P. aeruginosa* in presence of the outer membrane permeabilizer EDTA. However, in absence of EDTA, the antibacterial activity for three conventional fusion proteins dropped significantly. In contrast, the polypeptides according to the present invention retained again a significant level of antimicrobial activity even in absence of EDTA.

```
                      SEQUENCE LISTING

<160> NUMBER OF SEQ ID NOS: 125

<210> SEQ ID NO 1
<211> LENGTH: 164
<212> TYPE: PRT
<213> ORGANISM: Unknown
<220> FEATURE:
<223> OTHER INFORMATION: Endolysin derived from Citrobacter Koseri phage
      CkP1

<400> SEQUENCE: 1

Met Asn Ile Phe Lys Met Leu Arg Ile Asp Glu Gly Tyr Asp Ser Lys
1               5                   10                  15

Ile Tyr Lys Asp Thr Glu Gly Phe Trp Thr Ile Gly Ile Gly His Leu
            20                  25                  30

Leu Thr Arg Asp Pro Ser Leu Glu Val Ala Lys Arg Glu Leu Asp Lys
        35                  40                  45

Leu Val Gly Arg Lys Cys Asn Gly Gln Ile Thr Gln Ser Glu Ala Glu
    50                  55                  60

Lys Ile Phe Ala Asp Asp Val Asp Lys Ala Ile Asn Gly Ile Lys Lys
65                  70                  75                  80

Asn Ala Ser Leu Lys Pro Val Tyr Asp Ser Leu Asp Gly Asp Asp Pro
                85                  90                  95

Arg Gln Ala Ala Leu Ile Asn Met Val Phe Gln Met Gly Val Ala Gly
            100                 105                 110

Val Ala Gly Phe Thr Asn Ser Met Arg Met Val Lys Glu Lys Arg Trp
        115                 120                 125

Ala Asp Ala Ala Val Asn Leu Ala Gln Ser Lys Trp Tyr Arg Gln Thr
    130                 135                 140

Pro Asn Arg Ala Lys Arg Val Ile Glu Thr Phe Arg Thr Gly Thr Trp
145                 150                 155                 160

Asn Ala Tyr Lys

<210> SEQ ID NO 2
<211> LENGTH: 164
<212> TYPE: PRT
<213> ORGANISM: Enterobacteria phage CC31

<400> SEQUENCE: 2

Met Asp Ile Phe Gly Met Leu Arg Ile Asp Glu Gly Tyr Asp Ser Lys
1               5                   10                  15

Ile Tyr Lys Asp Thr Glu Gly Phe Trp Thr Ile Gly Ile Gly His Leu
            20                  25                  30

Leu Thr Arg Asp Pro Ser Leu Ala Val Ala Lys Arg Glu Leu Asp Lys
        35                  40                  45

Leu Val Gly Arg Pro Cys Asn Gly Gln Ile Thr Lys Ala Glu Ala Glu
    50                  55                  60

Ala Ile Phe Ala Lys Asp Val Asp Lys Ala Thr Arg Gly Ile Leu Gly
65                  70                  75                  80

Asn Ala Val Leu Lys Pro Val Tyr Asp Val Leu Asp Gly Val Arg Arg
                85                  90                  95

Ala Ala Leu Ile Asn Met Val Phe Gln Met Gly Val Ala Gly Val Ala
```

```
                100                 105                 110
Ser Phe Pro Ala Ser Met Arg Leu Leu Lys Ser Lys Gln Trp Glu Ala
            115                 120                 125

Ala Ala Lys Glu Leu Ala Asn Ser Lys Trp Tyr Arg Gln Thr Pro Asn
        130                 135                 140

Arg Ala Lys Arg Val Ile Ala Thr Phe Lys Thr Gly Thr Trp Lys Ala
145                 150                 155                 160

Tyr Glu Asn Leu

<210> SEQ ID NO 3
<211> LENGTH: 161
<212> TYPE: PRT
<213> ORGANISM: Serratia phage CHI14

<400> SEQUENCE: 3

Met Asp Ile Phe Gly Met Leu Arg Ile Asp Glu Gly Tyr Asp Ser Lys
1               5                   10                  15

Ile Tyr Lys Asp Thr Glu Gly Tyr Trp Thr Ile Gly Ile Gly His Leu
            20                  25                  30

Leu Thr Lys Asn Pro Ser Leu Ser Val Ala Lys Ala Glu Leu Asp Lys
        35                  40                  45

Leu Val Gly Arg Ser Cys Asn Gly Gln Ile Thr Gln Asp Glu Ala Glu
50                  55                  60

Ser Ile Phe Ala Lys Asp Val Glu Lys Ala Val Lys Gly Ile Gln Gly
65                  70                  75                  80

Asn Ser Val Leu Lys Pro Val Tyr Asp Ser Leu Asp Glu Ile Arg Arg
                85                  90                  95

Ala Ala Leu Ile Asn Met Val Phe Gln Met Gly Val Ala Gly Val Ala
            100                 105                 110

Gly Phe Thr Asn Ser Met Arg Met Leu Lys Glu Lys Arg Trp Asp Glu
        115                 120                 125

Ala Ala Val Asn Leu Ala Lys Ser Arg Trp Tyr Asn Gln Thr Thr Asn
    130                 135                 140

Arg Ala Lys Arg Val Ile Ser Thr Phe Lys Thr Gly Thr Trp Gly Ala
145                 150                 155                 160

Tyr

<210> SEQ ID NO 4
<211> LENGTH: 162
<212> TYPE: PRT
<213> ORGANISM: Unknown
<220> FEATURE:
<223> OTHER INFORMATION: Catalytic domain of endolysin derived from
      Citrobacter Koseri phage CkP1 w/o N-terminal methionine

<400> SEQUENCE: 4

Asn Ile Phe Lys Met Leu Arg Ile Asp Glu Gly Tyr Asp Ser Lys Ile
1               5                   10                  15

Tyr Lys Asp Thr Glu Gly Phe Trp Thr Ile Gly Ile Gly His Leu Leu
            20                  25                  30

Thr Arg Asp Pro Ser Leu Glu Val Ala Lys Arg Glu Leu Asp Lys Leu
        35                  40                  45

Val Gly Arg Lys Cys Asn Gly Gln Ile Thr Gln Ser Glu Ala Glu Lys
    50                  55                  60

Ile Phe Ala Asp Asp Val Asp Lys Ala Ile Asn Gly Ile Lys Lys Asn
65                  70                  75                  80
```

```
Ala Ser Leu Lys Pro Val Tyr Asp Ser Leu Asp Gly Asp Asp Pro Arg
                85                  90                  95

Gln Ala Ala Leu Ile Asn Met Val Phe Gln Met Gly Val Ala Gly Val
            100                 105                 110

Ala Gly Phe Thr Asn Ser Met Arg Met Val Lys Glu Lys Arg Trp Ala
        115                 120                 125

Asp Ala Ala Val Asn Leu Ala Gln Ser Lys Trp Tyr Arg Gln Thr Pro
    130                 135                 140

Asn Arg Ala Lys Arg Val Ile Glu Thr Phe Arg Thr Gly Thr Trp Asn
145                 150                 155                 160

Ala Tyr

<210> SEQ ID NO 5
<211> LENGTH: 163
<212> TYPE: PRT
<213> ORGANISM: Enterobacteria phage CC31

<400> SEQUENCE: 5

Asp Ile Phe Gly Met Leu Arg Ile Asp Glu Gly Tyr Asp Ser Lys Ile
1               5                   10                  15

Tyr Lys Asp Thr Glu Gly Phe Trp Thr Ile Gly Ile Gly His Leu Leu
            20                  25                  30

Thr Arg Asp Pro Ser Leu Asp Val Ala Lys Arg Glu Leu Asp Lys Leu
        35                  40                  45

Val Gly Arg Pro Cys Asn Gly Gln Ile Thr Lys Ala Glu Ala Glu Ala
    50                  55                  60

Ile Phe Ala Lys Asp Val Asp Lys Ala Thr Arg Gly Ile Leu Gly Asn
65                  70                  75                  80

Ala Val Leu Lys Pro Val Tyr Asp Val Leu Asp Gly Val Arg Arg Ala
                85                  90                  95

Ala Leu Ile Asn Met Val Phe Gln Met Gly Val Ala Gly Val Ala Ser
            100                 105                 110

Phe Pro Ala Ser Met Arg Leu Leu Lys Ser Lys Gln Trp Glu Ala Ala
        115                 120                 125

Ala Lys Glu Leu Ala Asn Ser Lys Trp Tyr Arg Gln Thr Pro Asn Arg
    130                 135                 140

Ala Lys Arg Val Ile Ala Thr Phe Lys Thr Gly Thr Trp Lys Ala Tyr
145                 150                 155                 160

Glu Asn Leu

<210> SEQ ID NO 6
<211> LENGTH: 160
<212> TYPE: PRT
<213> ORGANISM: phage CHI14

<400> SEQUENCE: 6

Asp Ile Phe Gly Met Leu Arg Ile Asp Glu Gly Tyr Asp Ser Lys Ile
1               5                   10                  15

Tyr Lys Asp Thr Glu Gly Tyr Trp Thr Ile Gly Ile Gly His Leu Leu
            20                  25                  30

Thr Lys Asn Pro Ser Leu Ser Val Ala Lys Ala Glu Leu Asp Lys Leu
        35                  40                  45

Val Gly Arg Ser Cys Asn Gly Gln Ile Thr Gln Asp Glu Ala Glu Ser
    50                  55                  60

Ile Phe Ala Lys Asp Val Glu Lys Ala Val Lys Gly Ile Gln Gly Asn
65                  70                  75                  80
```

```
Ser Val Leu Lys Pro Val Tyr Asp Ser Leu Asp Glu Ile Arg Arg Ala
                85                  90                  95

Ala Leu Ile Asn Met Val Phe Gln Met Gly Val Ala Gly Val Ala Gly
            100                 105                 110

Phe Thr Asn Ser Met Arg Met Leu Lys Glu Lys Arg Trp Asp Glu Ala
        115                 120                 125

Ala Val Asn Leu Ala Lys Ser Arg Trp Tyr Asn Gln Thr Thr Asn Arg
    130                 135                 140

Ala Lys Arg Val Ile Ser Thr Phe Lys Thr Gly Thr Trp Gly Ala Tyr
145                 150                 155                 160

<210> SEQ ID NO 7
<211> LENGTH: 163
<212> TYPE: PRT
<213> ORGANISM: Artificial sequence
<220> FEATURE:
<223> OTHER INFORMATION: Endolysin derived from Citrobacter Koseri phage
      CkP1, w/o N-terminal methionine and C54S

<400> SEQUENCE: 7

Asn Ile Phe Lys Met Leu Arg Ile Asp Glu Gly Tyr Asp Ser Lys Ile
1               5                   10                  15

Tyr Lys Asp Thr Glu Gly Phe Trp Thr Ile Gly Ile Gly His Leu Leu
            20                  25                  30

Thr Arg Asp Pro Ser Leu Glu Val Ala Lys Arg Glu Leu Asp Lys Leu
        35                  40                  45

Val Gly Arg Lys Ser Asn Gly Gln Ile Thr Gln Ser Glu Ala Glu Lys
    50                  55                  60

Ile Phe Ala Asp Asp Val Asp Lys Ala Ile Asn Gly Ile Lys Lys Asn
65                  70                  75                  80

Ala Ser Leu Lys Pro Val Tyr Asp Ser Leu Asp Gly Asp Asp Pro Arg
                85                  90                  95

Gln Ala Ala Leu Ile Asn Met Val Phe Gln Met Gly Val Ala Gly Val
            100                 105                 110

Ala Gly Phe Thr Asn Ser Met Arg Met Val Lys Glu Lys Arg Trp Ala
        115                 120                 125

Asp Ala Ala Val Asn Leu Ala Gln Ser Lys Trp Tyr Arg Gln Thr Pro
    130                 135                 140

Asn Arg Ala Lys Arg Val Ile Glu Thr Phe Arg Thr Gly Thr Trp Asn
145                 150                 155                 160

Ala Tyr Lys

<210> SEQ ID NO 8
<211> LENGTH: 163
<212> TYPE: PRT
<213> ORGANISM: Artificial sequence
<220> FEATURE:
<223> OTHER INFORMATION: Endolysin derived from Enterobacteria phage
      CC31, w/o N-terminal methionine and C54S

<400> SEQUENCE: 8

Asp Ile Phe Gly Met Leu Arg Ile Asp Glu Gly Tyr Asp Ser Lys Ile
1               5                   10                  15

Tyr Lys Asp Thr Glu Gly Phe Trp Thr Ile Gly Ile Gly His Leu Leu
            20                  25                  30

Thr Arg Asp Pro Ser Leu Asp Val Ala Lys Arg Glu Leu Asp Lys Leu
        35                  40                  45
```

Val Gly Arg Pro Ser Asn Gly Gln Ile Thr Lys Ala Glu Ala Glu Ala
    50                  55                  60

Ile Phe Ala Lys Asp Val Asp Lys Ala Thr Arg Gly Ile Leu Gly Asn
65                  70                  75                  80

Ala Val Leu Lys Pro Val Tyr Asp Val Leu Asp Gly Val Arg Arg Ala
                85                  90                  95

Ala Leu Ile Asn Met Val Phe Gln Met Gly Val Ala Gly Val Ala Ser
                100                 105                 110

Phe Pro Ala Ser Met Arg Leu Leu Lys Ser Lys Gln Trp Glu Ala Ala
            115                 120                 125

Ala Lys Glu Leu Ala Asn Ser Lys Trp Tyr Arg Gln Thr Pro Asn Arg
    130                 135                 140

Ala Lys Arg Val Ile Ala Thr Phe Lys Thr Gly Thr Trp Lys Ala Tyr
145                 150                 155                 160

Glu Asn Leu

<210> SEQ ID NO 9
<211> LENGTH: 160
<212> TYPE: PRT
<213> ORGANISM: Artificial sequence
<220> FEATURE:
<223> OTHER INFORMATION: Endolysin derived from phage CHI14, w/o
      N-terminal methionine and C54S

<400> SEQUENCE: 9

Asp Ile Phe Gly Met Leu Arg Ile Asp Glu Gly Tyr Asp Ser Lys Ile
1               5                   10                  15

Tyr Lys Asp Thr Glu Gly Tyr Trp Thr Ile Gly Ile Gly His Leu Leu
                20                  25                  30

Thr Lys Asn Pro Ser Leu Ser Val Ala Lys Ala Glu Leu Asp Lys Leu
            35                  40                  45

Val Gly Arg Ser Ser Asn Gly Gln Ile Thr Gln Asp Glu Ala Glu Ser
    50                  55                  60

Ile Phe Ala Lys Asp Val Glu Lys Ala Val Lys Gly Ile Gln Gly Asn
65                  70                  75                  80

Ser Val Leu Lys Pro Val Tyr Asp Ser Leu Asp Glu Ile Arg Arg Ala
                85                  90                  95

Ala Leu Ile Asn Met Val Phe Gln Met Gly Val Ala Gly Val Ala Gly
                100                 105                 110

Phe Thr Asn Ser Met Arg Met Leu Lys Glu Lys Arg Trp Asp Glu Ala
            115                 120                 125

Ala Val Asn Leu Ala Lys Ser Arg Trp Tyr Asn Gln Thr Thr Asn Arg
    130                 135                 140

Ala Lys Arg Val Ile Ser Thr Phe Lys Thr Gly Thr Trp Gly Ala Tyr
145                 150                 155                 160

<210> SEQ ID NO 10
<211> LENGTH: 184
<212> TYPE: PRT
<213> ORGANISM: Artificial sequence
<220> FEATURE:
<223> OTHER INFORMATION: Recombninant endolysin derived from Citrobacter
      Koseri phage CkP1 including N-terminal HisTag

<400> SEQUENCE: 10

Met Gly Ser Ser His His His His His His Ser Ser Gly Leu Val Pro
1               5                   10                  15

Arg Gly Ser His Met Asn Ile Phe Lys Met Leu Arg Ile Asp Glu Gly

```
                20                  25                  30
Tyr Asp Ser Lys Ile Tyr Lys Asp Thr Glu Gly Phe Trp Thr Ile Gly
            35                  40                  45

Ile Gly His Leu Leu Thr Arg Asp Pro Ser Leu Glu Val Ala Lys Arg
 50                  55                  60

Glu Leu Asp Lys Leu Val Gly Arg Lys Cys Asn Gly Gln Ile Thr Gln
 65                  70                  75                  80

Ser Glu Ala Glu Lys Ile Phe Ala Asp Asp Val Asp Lys Ala Ile Asn
                85                  90                  95

Gly Ile Lys Lys Asn Ala Ser Leu Lys Pro Val Tyr Asp Ser Leu Asp
            100                 105                 110

Gly Asp Asp Pro Arg Gln Ala Ala Leu Ile Asn Met Val Phe Gln Met
            115                 120                 125

Gly Val Ala Gly Val Ala Gly Phe Thr Asn Ser Met Arg Met Val Lys
        130                 135                 140

Glu Lys Arg Trp Ala Asp Ala Val Asn Leu Ala Gln Ser Lys Trp
145                 150                 155                 160

Tyr Arg Gln Thr Pro Asn Arg Ala Lys Arg Val Ile Glu Thr Phe Arg
                165                 170                 175

Thr Gly Thr Trp Asn Ala Tyr Lys
            180

<210> SEQ ID NO 11
<211> LENGTH: 6
<212> TYPE: PRT
<213> ORGANISM: artificial
<220> FEATURE:
<223> OTHER INFORMATION: synthetic sequence

<400> SEQUENCE: 11

Lys Arg Lys Lys Arg Lys
1               5

<210> SEQ ID NO 12
<211> LENGTH: 5
<212> TYPE: PRT
<213> ORGANISM: artificial
<220> FEATURE:
<223> OTHER INFORMATION: synethtic sequence
<220> FEATURE:
<221> NAME/KEY: misc_feature
<222> LOCATION: (3)..(3)
<223> OTHER INFORMATION: Xaa can be any naturally occurring amino acid

<400> SEQUENCE: 12

Lys Arg Xaa Lys Arg
1               5

<210> SEQ ID NO 13
<211> LENGTH: 5
<212> TYPE: PRT
<213> ORGANISM: artificial
<220> FEATURE:
<223> OTHER INFORMATION: synthetic sequence

<400> SEQUENCE: 13

Lys Arg Ser Lys Arg
1               5

<210> SEQ ID NO 14
<211> LENGTH: 5
<212> TYPE: PRT
```

<213> ORGANISM: artificial
<220> FEATURE:
<223> OTHER INFORMATION: synthetic sequence

<400> SEQUENCE: 14

Lys Arg Gly Ser Gly
1               5

<210> SEQ ID NO 15
<211> LENGTH: 9
<212> TYPE: PRT
<213> ORGANISM: artificial
<220> FEATURE:
<223> OTHER INFORMATION: synthetic sequence

<400> SEQUENCE: 15

Lys Arg Lys Lys Arg Lys Lys Arg Lys
1               5

<210> SEQ ID NO 16
<211> LENGTH: 9
<212> TYPE: PRT
<213> ORGANISM: artificial
<220> FEATURE:
<223> OTHER INFORMATION: synthetic sequence

<400> SEQUENCE: 16

Arg Arg Arg Arg Arg Arg Arg Arg Arg
1               5

<210> SEQ ID NO 17
<211> LENGTH: 8
<212> TYPE: PRT
<213> ORGANISM: artificial
<220> FEATURE:
<223> OTHER INFORMATION: synthetic sequence

<400> SEQUENCE: 17

Lys Lys Lys Lys Lys Lys Lys Lys
1               5

<210> SEQ ID NO 18
<211> LENGTH: 10
<212> TYPE: PRT
<213> ORGANISM: artificial
<220> FEATURE:
<223> OTHER INFORMATION: synthetic sequence

<400> SEQUENCE: 18

Lys Arg Lys Lys Arg Lys Lys Arg Lys Lys
1               5                   10

<210> SEQ ID NO 19
<211> LENGTH: 12
<212> TYPE: PRT
<213> ORGANISM: artificial
<220> FEATURE:
<223> OTHER INFORMATION: synthetic sequence

<400> SEQUENCE: 19

Lys Arg Lys Lys Arg Lys Lys Arg Lys Lys Arg Lys
1               5                   10

<210> SEQ ID NO 20
<211> LENGTH: 14
<212> TYPE: PRT
<213> ORGANISM: artificial

<220> FEATURE:
<223> OTHER INFORMATION: synthetic sequence

<400> SEQUENCE: 20

Lys Arg Lys Lys Arg Lys Lys Arg Lys Lys Arg Lys Lys Arg
1               5                   10

<210> SEQ ID NO 21
<211> LENGTH: 16
<212> TYPE: PRT
<213> ORGANISM: artificial
<220> FEATURE:
<223> OTHER INFORMATION: synthetic sequence

<400> SEQUENCE: 21

Lys Lys Lys Lys Lys Lys Lys Lys Lys Lys Lys Lys Lys Lys Lys Lys
1               5                   10                  15

<210> SEQ ID NO 22
<211> LENGTH: 18
<212> TYPE: PRT
<213> ORGANISM: artificial
<220> FEATURE:
<223> OTHER INFORMATION: synthetic sequence

<400> SEQUENCE: 22

Lys Arg Lys Lys Arg Lys Lys Arg Lys Lys Arg Lys Lys Arg Lys Lys
1               5                   10                  15

Arg Lys

<210> SEQ ID NO 23
<211> LENGTH: 19
<212> TYPE: PRT
<213> ORGANISM: artificial
<220> FEATURE:
<223> OTHER INFORMATION: synthetic sequence

<400> SEQUENCE: 23

Lys Arg Lys Lys Arg Lys Lys Arg Lys Lys Arg Lys Lys Arg Lys Lys
1               5                   10                  15

Arg Lys Lys

<210> SEQ ID NO 24
<211> LENGTH: 19
<212> TYPE: PRT
<213> ORGANISM: artificial
<220> FEATURE:
<223> OTHER INFORMATION: synthetic sequence

<400> SEQUENCE: 24

Arg Arg Arg Arg Arg Arg Arg Arg Arg Arg Arg Arg Arg Arg Arg Arg
1               5                   10                  15

Arg Arg Arg

<210> SEQ ID NO 25
<211> LENGTH: 19
<212> TYPE: PRT
<213> ORGANISM: artificial
<220> FEATURE:
<223> OTHER INFORMATION: synthetic sequence

<400> SEQUENCE: 25

Lys Lys Lys Lys Lys Lys Lys Lys Lys Lys Lys Lys Lys Lys Lys Lys
1               5                   10                  15

Lys Lys Lys

<210> SEQ ID NO 26
<211> LENGTH: 20
<212> TYPE: PRT
<213> ORGANISM: artificial
<220> FEATURE:
<223> OTHER INFORMATION: synthetic sequence

<400> SEQUENCE: 26

Lys Arg Lys Lys Arg Lys Lys Arg Lys Arg Ser Lys Arg Lys Lys Arg
1               5                   10                  15

Lys Lys Arg Lys
            20

<210> SEQ ID NO 27
<211> LENGTH: 21
<212> TYPE: PRT
<213> ORGANISM: artificial
<220> FEATURE:
<223> OTHER INFORMATION: synthetic sequence

<400> SEQUENCE: 27

Lys Arg Lys Lys Arg Lys Lys Arg Lys Arg Ser Lys Arg Lys Lys Arg
1               5                   10                  15

Lys Lys Arg Lys Lys
            20

<210> SEQ ID NO 28
<211> LENGTH: 21
<212> TYPE: PRT
<213> ORGANISM: artificial
<220> FEATURE:
<223> OTHER INFORMATION: synthetic sequence

<400> SEQUENCE: 28

Lys Arg Lys Lys Arg Lys Lys Arg Lys Lys Arg Lys Lys Arg Lys Lys
1               5                   10                  15

Arg Lys Lys Arg Lys
            20

<210> SEQ ID NO 29
<211> LENGTH: 22
<212> TYPE: PRT
<213> ORGANISM: artificial
<220> FEATURE:
<223> OTHER INFORMATION: synthetic sequence

<400> SEQUENCE: 29

Lys Arg Lys Lys Arg Lys Lys Arg Lys Arg Gly Ser Gly Lys Arg Lys
1               5                   10                  15

Lys Arg Lys Lys Arg Lys
            20

<210> SEQ ID NO 30
<211> LENGTH: 24
<212> TYPE: PRT
<213> ORGANISM: artificial
<220> FEATURE:
<223> OTHER INFORMATION: synthetic sequence

<400> SEQUENCE: 30

Lys Arg Lys Lys Arg Lys Lys Arg Lys Arg Gly Ser Gly Ser Gly Lys
1               5                   10                  15

-continued

Arg Lys Lys Arg Lys Lys Arg Lys
            20

<210> SEQ ID NO 31
<211> LENGTH: 25
<212> TYPE: PRT
<213> ORGANISM: artificial
<220> FEATURE:
<223> OTHER INFORMATION: synthetic sequence

<400> SEQUENCE: 31

Lys Arg Lys Lys Arg Lys Lys Arg Lys Arg Lys Lys Arg Lys Lys
1               5                   10                  15

Arg Lys Lys Arg Lys Lys Arg Lys Lys
            20                  25

<210> SEQ ID NO 32
<211> LENGTH: 31
<212> TYPE: PRT
<213> ORGANISM: artificial
<220> FEATURE:
<223> OTHER INFORMATION: synthetic sequence

<400> SEQUENCE: 32

Lys Arg Lys Lys Arg Lys Lys Arg Lys Arg Ser Lys Arg Lys Lys Arg
1               5                   10                  15

Lys Lys Arg Lys Arg Ser Lys Arg Lys Lys Arg Lys Lys Arg Lys
            20                  25                  30

<210> SEQ ID NO 33
<211> LENGTH: 38
<212> TYPE: PRT
<213> ORGANISM: artificial
<220> FEATURE:
<223> OTHER INFORMATION: synthetic sequence

<400> SEQUENCE: 33

Lys Arg Lys Lys Arg Lys Lys Arg Lys Arg Gly Ser Gly Ser Gly Lys
1               5                   10                  15

Arg Lys Lys Arg Lys Lys Arg Lys Gly Ser Gly Ser Gly Lys Arg Lys
            20                  25                  30

Lys Arg Lys Lys Arg Lys
        35

<210> SEQ ID NO 34
<211> LENGTH: 39
<212> TYPE: PRT
<213> ORGANISM: artificial
<220> FEATURE:
<223> OTHER INFORMATION: synthetic sequence

<400> SEQUENCE: 34

Lys Arg Lys Lys Arg Lys Lys Arg Lys Lys Arg Lys Lys Arg Lys Lys
1               5                   10                  15

Arg Lys Lys Arg Lys Lys Arg Lys Lys Arg Lys Lys Arg Lys Lys Arg
            20                  25                  30

Lys Lys Arg Lys Lys Arg Lys
        35

<210> SEQ ID NO 35
<211> LENGTH: 42
<212> TYPE: PRT
<213> ORGANISM: artificial
<220> FEATURE:

-continued

<223> OTHER INFORMATION: synthetic sequence

<400> SEQUENCE: 35

Lys Arg Lys Lys Arg Lys Lys Arg Lys Ser Lys Arg Lys Lys Arg
1               5                   10                  15

Lys Lys Arg Lys Arg Ser Lys Arg Lys Lys Arg Lys Lys Arg Lys Arg
            20                  25                  30

Ser Lys Arg Lys Lys Arg Lys Lys Arg Lys
        35                  40

<210> SEQ ID NO 36
<211> LENGTH: 37
<212> TYPE: PRT
<213> ORGANISM: Homo sapiens

<400> SEQUENCE: 36

Leu Leu Gly Asp Phe Phe Arg Lys Ser Lys Glu Lys Ile Gly Lys Glu
1               5                   10                  15

Phe Lys Arg Ile Val Gln Arg Ile Lys Asp Phe Leu Arg Asn Leu Val
            20                  25                  30

Pro Arg Thr Glu Ser
        35

<210> SEQ ID NO 37
<211> LENGTH: 29
<212> TYPE: PRT
<213> ORGANISM: unknown
<220> FEATURE:
<223> OTHER INFORMATION: SMAP-29 sheep

<400> SEQUENCE: 37

Arg Gly Leu Arg Arg Leu Gly Arg Lys Ile Ala His Gly Val Lys Lys
1               5                   10                  15

Tyr Gly Pro Thr Val Leu Arg Ile Ile Arg Ile Ala Gly
            20                  25

<210> SEQ ID NO 38
<211> LENGTH: 13
<212> TYPE: PRT
<213> ORGANISM: unknown
<220> FEATURE:
<223> OTHER INFORMATION: Indolicidine bovine

<400> SEQUENCE: 38

Ile Leu Pro Trp Lys Trp Pro Trp Trp Pro Trp Arg Arg
1               5                   10

<210> SEQ ID NO 39
<211> LENGTH: 18
<212> TYPE: PRT
<213> ORGANISM: unknown
<220> FEATURE:
<223> OTHER INFORMATION: Protegrin Porcine

<400> SEQUENCE: 39

Arg Gly Gly Arg Leu Cys Tyr Cys Arg Arg Arg Phe Cys Val Cys Val
1               5                   10                  15

Gly Arg

<210> SEQ ID NO 40
<211> LENGTH: 31
<212> TYPE: PRT
<213> ORGANISM: unknown

```
<220> FEATURE:
<223> OTHER INFORMATION: Cecropin P1 Mammal (pig)

<400> SEQUENCE: 40

Ser Trp Leu Ser Lys Thr Ala Lys Lys Leu Glu Asn Ser Ala Lys Lys
1               5                   10                  15

Arg Ile Ser Glu Gly Ile Ala Ile Ala Ile Gln Gly Gly Pro Arg
            20                  25                  30

<210> SEQ ID NO 41
<211> LENGTH: 23
<212> TYPE: PRT
<213> ORGANISM: unknown
<220> FEATURE:
<223> OTHER INFORMATION: Magainin frog

<400> SEQUENCE: 41

Gly Ile Gly Lys Phe Leu His Ser Ala Lys Lys Phe Gly Lys Ala Phe
1               5                   10                  15

Val Gly Glu Ile Met Asn Ser
            20

<210> SEQ ID NO 42
<211> LENGTH: 25
<212> TYPE: PRT
<213> ORGANISM: unknown
<220> FEATURE:
<223> OTHER INFORMATION: Pleurocidin fish

<400> SEQUENCE: 42

Gly Trp Gly Ser Phe Phe Lys Lys Ala Ala His Val Gly Lys His Val
1               5                   10                  15

Gly Lys Ala Ala Leu Thr His Tyr Leu
            20                  25

<210> SEQ ID NO 43
<211> LENGTH: 36
<212> TYPE: PRT
<213> ORGANISM: Aedes aegypti

<400> SEQUENCE: 43

Gly Gly Leu Lys Lys Leu Gly Lys Lys Leu Glu Gly Ala Gly Lys Arg
1               5                   10                  15

Val Phe Asn Ala Ala Glu Lys Ala Leu Pro Val Val Ala Gly Ala Lys
            20                  25                  30

Ala Leu Arg Lys
        35

<210> SEQ ID NO 44
<211> LENGTH: 40
<212> TYPE: PRT
<213> ORGANISM: Drosophila melanogaster

<400> SEQUENCE: 44

Gly Trp Leu Lys Lys Ile Gly Lys Lys Ile Glu Arg Val Gly Gln His
1               5                   10                  15

Thr Arg Asp Ala Thr Ile Gln Gly Leu Gly Ile Pro Gln Gln Ala Ala
            20                  25                  30

Asn Val Ala Ala Thr Ala Arg Gly
        35                  40

<210> SEQ ID NO 45
```

```
<211> LENGTH: 21
<212> TYPE: PRT
<213> ORGANISM: unknown
<220> FEATURE:
<223> OTHER INFORMATION: Buforin II vertebrate

<400> SEQUENCE: 45

Thr Arg Ser Ser Arg Ala Gly Leu Gln Phe Pro Val Gly Arg Val His
1               5                   10                  15

Arg Leu Leu Arg Lys
            20

<210> SEQ ID NO 46
<211> LENGTH: 39
<212> TYPE: PRT
<213> ORGANISM: unknown
<220> FEATURE:
<223> OTHER INFORMATION: Sarcotoxin IA Fly

<400> SEQUENCE: 46

Gly Trp Leu Lys Lys Ile Gly Lys Lys Ile Glu Arg Val Gly Gln His
1               5                   10                  15

Thr Arg Asp Ala Thr Ile Gln Gly Leu Gly Ile Ala Gln Gln Ala Ala
            20                  25                  30

Asn Val Ala Ala Thr Ala Arg
        35

<210> SEQ ID NO 47
<211> LENGTH: 17
<212> TYPE: PRT
<213> ORGANISM: Apis mellifera

<400> SEQUENCE: 47

Ala Asn Arg Pro Val Tyr Ile Pro Pro Pro Arg Pro Pro His Pro Arg
1               5                   10                  15

Leu

<210> SEQ ID NO 48
<211> LENGTH: 24
<212> TYPE: PRT
<213> ORGANISM: unknown
<220> FEATURE:
<223> OTHER INFORMATION: Ascaphine 5 Frog

<400> SEQUENCE: 48

Gly Ile Lys Asp Trp Ile Lys Gly Ala Ala Lys Lys Leu Ile Lys Thr
1               5                   10                  15

Val Ala Ser His Ile Ala Asn Gln
            20

<210> SEQ ID NO 49
<211> LENGTH: 22
<212> TYPE: PRT
<213> ORGANISM: unknown
<220> FEATURE:
<223> OTHER INFORMATION: Nigrocine 2 Frog

<400> SEQUENCE: 49

Gly Leu Leu Ser Lys Val Leu Gly Val Gly Lys Lys Val Leu Cys Gly
1               5                   10                  15

Val Ser Gly Leu Val Cys
            20
```

```
<210> SEQ ID NO 50
<211> LENGTH: 24
<212> TYPE: PRT
<213> ORGANISM: unknown
<220> FEATURE:
<223> OTHER INFORMATION: Pseudin 1 Rana Frog

<400> SEQUENCE: 50

Gly Leu Asn Thr Leu Lys Lys Val Phe Gln Gly Leu His Glu Ala Ile
1               5                   10                  15

Lys Leu Ile Asn Asn His Val Gln
            20

<210> SEQ ID NO 51
<211> LENGTH: 18
<212> TYPE: PRT
<213> ORGANISM: unknown
<220> FEATURE:
<223> OTHER INFORMATION: Ranalexin Frog

<400> SEQUENCE: 51

Phe Leu Gly Gly Leu Ile Val Pro Ala Met Ile Cys Ala Val Thr Lys
1               5                   10                  15

Lys Cys

<210> SEQ ID NO 52
<211> LENGTH: 26
<212> TYPE: PRT
<213> ORGANISM: unknown
<220> FEATURE:
<223> OTHER INFORMATION: Melittin bee

<400> SEQUENCE: 52

Gly Ile Gly Ala Val Leu Lys Val Leu Thr Thr Gly Leu Pro Ala Leu
1               5                   10                  15

Ile Ser Trp Ile Lys Arg Lys Arg Gln Gln
            20                  25

<210> SEQ ID NO 53
<211> LENGTH: 25
<212> TYPE: PRT
<213> ORGANISM: unknown
<220> FEATURE:
<223> OTHER INFORMATION: Lycotoxin 1 Spider

<400> SEQUENCE: 53

Ile Trp Leu Thr Ala Leu Lys Phe Leu Gly Lys His Ala Ala Lys Lys
1               5                   10                  15

Leu Ala Lys Gln Gln Leu Ser Lys Leu
            20                  25

<210> SEQ ID NO 54
<211> LENGTH: 19
<212> TYPE: PRT
<213> ORGANISM: unknown
<220> FEATURE:
<223> OTHER INFORMATION: Parasin 1 Fish

<400> SEQUENCE: 54

Lys Gly Arg Gly Lys Gln Gly Gly Lys Val Arg Ala Lys Ala Lys Thr
1               5                   10                  15

Arg Ser Ser

<210> SEQ ID NO 55
```

```
<211> LENGTH: 39
<212> TYPE: PRT
<213> ORGANISM: unknown
<220> FEATURE:
<223> OTHER INFORMATION: Buforin I Toad

<400> SEQUENCE: 55

Ala Gly Arg Gly Lys Gln Gly Gly Lys Val Arg Ala Lys Ala Lys Thr
1               5                   10                  15
Arg Ser Ser Arg Ala Gly Leu Gln Phe Pro Val Gly Arg Val His Arg
            20                  25                  30
Leu Leu Arg Lys Gly Asn Tyr
        35

<210> SEQ ID NO 56
<211> LENGTH: 34
<212> TYPE: PRT
<213> ORGANISM: unknown
<220> FEATURE:
<223> OTHER INFORMATION: Dermaseptin 1 Frog

<400> SEQUENCE: 56

Ala Leu Trp Lys Thr Met Leu Lys Lys Leu Gly Thr Met Ala Leu His
1               5                   10                  15
Ala Gly Lys Ala Ala Leu Gly Ala Ala Ala Asp Thr Ile Ser Gln Gly
            20                  25                  30
Thr Gln

<210> SEQ ID NO 57
<211> LENGTH: 12
<212> TYPE: PRT
<213> ORGANISM: unknown
<220> FEATURE:
<223> OTHER INFORMATION: Bactenecin 1 Cow

<400> SEQUENCE: 57

Arg Leu Cys Arg Ile Val Val Ile Arg Val Cys Arg
1               5                   10

<210> SEQ ID NO 58
<211> LENGTH: 21
<212> TYPE: PRT
<213> ORGANISM: unknown
<220> FEATURE:
<223> OTHER INFORMATION: Thanatin Insect

<400> SEQUENCE: 58

Gly Ser Lys Lys Pro Val Pro Ile Ile Tyr Cys Asn Arg Arg Thr Gly
1               5                   10                  15
Lys Cys Gln Arg Met
            20

<210> SEQ ID NO 59
<211> LENGTH: 19
<212> TYPE: PRT
<213> ORGANISM: unknown
<220> FEATURE:
<223> OTHER INFORMATION: Brevinin 1T Rana frogs

<400> SEQUENCE: 59

Val Asn Pro Ile Ile Leu Gly Val Leu Pro Lys Val Cys Leu Ile Thr
1               5                   10                  15
Lys Lys Cys
```

-continued

<210> SEQ ID NO 60
<211> LENGTH: 26
<212> TYPE: PRT
<213> ORGANISM: unknown
<220> FEATURE:
<223> OTHER INFORMATION: Ranateurin 1 Rana frog

<400> SEQUENCE: 60

Ser Met Leu Ser Val Leu Lys Asn Leu Gly Lys Val Gly Leu Gly Phe
1               5                   10                  15

Val Ala Cys Lys Ile Asn Ile Lys Gln Cys
            20                  25

<210> SEQ ID NO 61
<211> LENGTH: 46
<212> TYPE: PRT
<213> ORGANISM: unknown
<220> FEATURE:
<223> OTHER INFORMATION: Esculentin 1 Rana frogs

<400> SEQUENCE: 61

Gly Ile Phe Ser Lys Leu Gly Arg Lys Lys Ile Lys Asn Leu Leu Ile
1               5                   10                  15

Ser Gly Leu Lys Asn Val Gly Lys Glu Val Gly Met Asp Val Val Arg
                20                  25                  30

Thr Gly Ile Lys Ile Ala Gly Cys Lys Ile Lys Gly Glu Cys
        35                  40                  45

<210> SEQ ID NO 62
<211> LENGTH: 17
<212> TYPE: PRT
<213> ORGANISM: Limulus polyphemus

<400> SEQUENCE: 62

Arg Trp Cys Phe Arg Val Cys Tyr Arg Gly Ile Cys Tyr Arg Lys Cys
1               5                   10                  15

Arg

<210> SEQ ID NO 63
<211> LENGTH: 25
<212> TYPE: PRT
<213> ORGANISM: unknown
<220> FEATURE:
<223> OTHER INFORMATION: Androctonin Scorpion

<400> SEQUENCE: 63

Arg Ser Val Cys Arg Gln Ile Lys Ile Cys Arg Arg Arg Gly Gly Cys
1               5                   10                  15

Tyr Tyr Lys Cys Thr Asn Arg Pro Tyr
            20                  25

<210> SEQ ID NO 64
<211> LENGTH: 30
<212> TYPE: PRT
<213> ORGANISM: Homo sapiens

<400> SEQUENCE: 64

Asp Cys Tyr Cys Arg Ile Pro Ala Cys Ile Ala Gly Glu Arg Arg Tyr
1               5                   10                  15

Gly Thr Cys Ile Tyr Gln Gly Arg Leu Trp Ala Phe Cys Cys
            20                  25                  30

```
<210> SEQ ID NO 65
<211> LENGTH: 38
<212> TYPE: PRT
<213> ORGANISM: unknown
<220> FEATURE:
<223> OTHER INFORMATION: beta-defensin cow

<400> SEQUENCE: 65

Asn Pro Val Ser Cys Val Arg Asn Lys Gly Ile Cys Val Pro Ile Arg
1               5                   10                  15

Cys Pro Gly Ser Met Lys Gln Ile Gly Thr Cys Val Gly Arg Ala Val
                20                  25                  30

Lys Cys Cys Arg Lys Lys
        35

<210> SEQ ID NO 66
<211> LENGTH: 18
<212> TYPE: PRT
<213> ORGANISM: unknown
<220> FEATURE:
<223> OTHER INFORMATION: theta-defensin monkey

<400> SEQUENCE: 66

Gly Phe Cys Arg Cys Leu Cys Arg Arg Gly Val Cys Arg Cys Ile Cys
1               5                   10                  15

Thr Arg

<210> SEQ ID NO 67
<211> LENGTH: 40
<212> TYPE: PRT
<213> ORGANISM: unknown
<220> FEATURE:
<223> OTHER INFORMATION: defensin (sapecin A) insect

<400> SEQUENCE: 67

Ala Thr Cys Asp Leu Leu Ser Gly Thr Gly Ile Asn His Ser Ala Cys
1               5                   10                  15

Ala Ala His Cys Leu Leu Arg Gly Asn Arg Gly Gly Tyr Cys Asn Gly
                20                  25                  30

Lys Ala Val Cys Val Cys Arg Asn
        35                  40

<210> SEQ ID NO 68
<211> LENGTH: 46
<212> TYPE: PRT
<213> ORGANISM: unknown
<220> FEATURE:
<223> OTHER INFORMATION: Thionin (crambin) plant

<400> SEQUENCE: 68

Thr Thr Cys Cys Pro Ser Ile Val Ala Arg Ser Asn Phe Asn Val Cys
1               5                   10                  15

Arg Ile Pro Gly Thr Pro Glu Ala Ile Cys Ala Thr Tyr Thr Gly Cys
                20                  25                  30

Ile Ile Ile Pro Gly Ala Thr Cys Pro Gly Asp Tyr Ala Asn
        35                  40                  45

<210> SEQ ID NO 69
<211> LENGTH: 50
<212> TYPE: PRT
<213> ORGANISM: unknown
<220> FEATURE:
<223> OTHER INFORMATION: defensin from radish
```

```
<400> SEQUENCE: 69

Gln Lys Leu Cys Gln Arg Pro Ser Gly Thr Trp Ser Gly Val Cys Gly
1               5                   10                  15

Asn Asn Asn Ala Cys Lys Asn Gln Cys Ile Arg Leu Glu Lys Ala Arg
            20                  25                  30

His Gly Ser Cys Asn Tyr Val Phe Pro Ala His Cys Ile Cys Tyr Phe
        35                  40                  45

Pro Cys
    50

<210> SEQ ID NO 70
<211> LENGTH: 30
<212> TYPE: PRT
<213> ORGANISM: Bungarus fasciatus

<400> SEQUENCE: 70

Lys Phe Phe Arg Lys Leu Lys Lys Ser Val Lys Lys Arg Ala Lys Glu
1               5                   10                  15

Phe Phe Lys Lys Pro Arg Val Ile Gly Val Ser Ile Pro Phe
            20                  25                  30

<210> SEQ ID NO 71
<211> LENGTH: 44
<212> TYPE: PRT
<213> ORGANISM: Drosophila melanogaster

<400> SEQUENCE: 71

Asp Cys Leu Ser Gly Arg Tyr Lys Gly Pro Cys Ala Val Trp Asp Asn
1               5                   10                  15

Glu Thr Cys Arg Arg Val Cys Lys Glu Glu Gly Arg Ser Ser Gly His
            20                  25                  30

Cys Ser Pro Ser Leu Lys Cys Trp Cys Glu Gly Cys
        35                  40

<210> SEQ ID NO 72
<211> LENGTH: 25
<212> TYPE: PRT
<213> ORGANISM: Homo sapiens

<400> SEQUENCE: 72

Asp Thr His Phe Pro Ile Cys Ile Phe Cys Cys Gly Cys Cys His Arg
1               5                   10                  15

Ser Lys Cys Gly Met Cys Cys Lys Thr
            20                  25

<210> SEQ ID NO 73
<211> LENGTH: 44
<212> TYPE: PRT
<213> ORGANISM: unknown
<220> FEATURE:
<223> OTHER INFORMATION: Bac 5 Cow

<400> SEQUENCE: 73

Arg Phe Arg Pro Pro Ile Arg Arg Pro Pro Ile Arg Pro Pro Phe Tyr
1               5                   10                  15

Pro Pro Phe Arg Pro Pro Ile Arg Pro Pro Ile Phe Pro Pro Ile Arg
            20                  25                  30

Pro Pro Phe Arg Pro Pro Leu Gly Arg Pro Phe Pro
        35                  40
```

-continued

```
<210> SEQ ID NO 74
<211> LENGTH: 39
<212> TYPE: PRT
<213> ORGANISM: unknown
<220> FEATURE:
<223> OTHER INFORMATION: PR-39 Pig

<400> SEQUENCE: 74

Arg Arg Arg Pro Arg Pro Pro Tyr Leu Pro Arg Pro Arg Pro Pro
1               5                   10                  15

Phe Phe Pro Pro Arg Leu Pro Pro Arg Ile Pro Pro Gly Phe Pro Pro
            20                  25                  30

Arg Phe Pro Pro Arg Phe Pro
        35

<210> SEQ ID NO 75
<211> LENGTH: 20
<212> TYPE: PRT
<213> ORGANISM: unknown
<220> FEATURE:
<223> OTHER INFORMATION: Pyrrhocoricin Insect

<400> SEQUENCE: 75

Val Asp Lys Gly Ser Tyr Leu Pro Arg Pro Thr Pro Pro Arg Pro Ile
1               5                   10                  15

Tyr Asn Arg Asn
        20

<210> SEQ ID NO 76
<211> LENGTH: 24
<212> TYPE: PRT
<213> ORGANISM: Homo sapiens

<400> SEQUENCE: 76

Asp Ser His Ala Lys Arg His His Gly Tyr Lys Arg Lys Phe His Glu
1               5                   10                  15

Lys His His Ser His Arg Gly Tyr
        20

<210> SEQ ID NO 77
<211> LENGTH: 19
<212> TYPE: PRT
<213> ORGANISM: Unknown
<220> FEATURE:
<223> OTHER INFORMATION: ECP19

<400> SEQUENCE: 77

Arg Pro Pro Gln Phe Thr Arg Ala Gln Trp Phe Ala Ile Gln His Ile
1               5                   10                  15

Ser Leu Asn

<210> SEQ ID NO 78
<211> LENGTH: 23
<212> TYPE: PRT
<213> ORGANISM: Unknown
<220> FEATURE:
<223> OTHER INFORMATION: MSI-594

<400> SEQUENCE: 78

Gly Ile Gly Lys Phe Leu Lys Lys Ala Lys Lys Gly Ile Gly Ala Val
1               5                   10                  15

Leu Lys Val Leu Thr Thr Gly
        20
```

```
<210> SEQ ID NO 79
<211> LENGTH: 35
<212> TYPE: PRT
<213> ORGANISM: Unknown
<220> FEATURE:
<223> OTHER INFORMATION: TL-ColM

<400> SEQUENCE: 79

Met Glu Thr Leu Thr Val His Ala Pro Ser Pro Ser Thr Asn Leu Pro
1               5                   10                  15

Ser Tyr Gly Asn Gly Ala Phe Ser Leu Ser Ala Pro His Val Pro Gly
            20                  25                  30

Ala Gly Pro
        35

<210> SEQ ID NO 80
<211> LENGTH: 18
<212> TYPE: PRT
<213> ORGANISM: Unknown
<220> FEATURE:
<223> OTHER INFORMATION: SBO

<400> SEQUENCE: 80

Lys Leu Lys Lys Ile Ala Gln Lys Ile Lys Asn Phe Phe Ala Lys Leu
1               5                   10                  15

Val Ala

<210> SEQ ID NO 81
<211> LENGTH: 30
<212> TYPE: PRT
<213> ORGANISM: Artificial sequence
<220> FEATURE:
<223> OTHER INFORMATION: synthetic sequence

<400> SEQUENCE: 81

Lys Phe Phe Arg Lys Leu Lys Lys Ser Val Lys Lys Arg Ala Lys Arg
1               5                   10                  15

Phe Phe Lys Lys Pro Arg Val Ile Gly Val Ser Ile Pro Phe
            20                  25                  30

<210> SEQ ID NO 82
<211> LENGTH: 34
<212> TYPE: PRT
<213> ORGANISM: Limulus polyphemus

<400> SEQUENCE: 82

Gly Phe Lys Leu Lys Gly Met Ala Arg Ile Ser Cys Leu Pro Asn Gly
1               5                   10                  15

Gln Trp Ser Asn Phe Pro Pro Lys Cys Ile Arg Glu Cys Ala Met Val
            20                  25                  30

Ser Ser

<210> SEQ ID NO 83
<211> LENGTH: 27
<212> TYPE: PRT
<213> ORGANISM: artificial
<220> FEATURE:
<223> OTHER INFORMATION: synthetic sequence

<400> SEQUENCE: 83

Lys Arg Trp Val Lys Arg Val Lys Arg Val Lys Arg Trp Val Lys Arg
1               5                   10                  15
```

```
Val Val Arg Val Val Lys Arg Trp Val Lys Arg
            20                  25

<210> SEQ ID NO 84
<211> LENGTH: 25
<212> TYPE: PRT
<213> ORGANISM: Artificial Sequence
<220> FEATURE:
<223> OTHER INFORMATION: synthetic sequence; MW2

<400> SEQUENCE: 84

Gly Lys Pro Gly Trp Leu Ile Lys Val Ala Leu Lys Phe Lys Leu
1               5                   10                  15

Ile Arg Arg Pro Leu Lys Arg Leu Ala
            20                  25

<210> SEQ ID NO 85
<211> LENGTH: 5
<212> TYPE: PRT
<213> ORGANISM: Artificial sequence
<220> FEATURE:
<223> OTHER INFORMATION: sequence, which is not part of the sequence
      motif, if the sequence motif contains at least three non-adjacent
      histidine residues

<400> SEQUENCE: 85

Ala Ala Leu Thr His
1               5

<210> SEQ ID NO 86
<211> LENGTH: 4
<212> TYPE: PRT
<213> ORGANISM: Artificial sequence
<220> FEATURE:
<223> OTHER INFORMATION: Example for intrasequential pairwise block of
      amino acids of the first group

<400> SEQUENCE: 86

Leu Lys Arg Glu
1

<210> SEQ ID NO 87
<211> LENGTH: 5
<212> TYPE: PRT
<213> ORGANISM: Artificial sequence
<220> FEATURE:
<223> OTHER INFORMATION: Example for intrasequential triplet block of
      amino acids of the first group

<400> SEQUENCE: 87

Leu Lys Arg Lys Glu
1               5

<210> SEQ ID NO 88
<211> LENGTH: 4
<212> TYPE: PRT
<213> ORGANISM: Artificial sequence
<220> FEATURE:
<223> OTHER INFORMATION: Example for N-terminal triplet block of amino
      acids of the first group

<400> SEQUENCE: 88

Lys Arg Lys Glu
1

<210> SEQ ID NO 89
<211> LENGTH: 4
```

```
<212> TYPE: PRT
<213> ORGANISM: Artificial sequence
<220> FEATURE:
<223> OTHER INFORMATION: Example for C-terminal triplet block of amino
      acids of the first group

<400> SEQUENCE: 89

Leu Lys Arg Lys
1

<210> SEQ ID NO 90
<211> LENGTH: 7
<212> TYPE: PRT
<213> ORGANISM: Artificial sequence
<220> FEATURE:
<223> OTHER INFORMATION: Example of a sequence precluded from the
      sequence motif, if a triplet of amnio acids of the first group is
      present

<400> SEQUENCE: 90

Arg Arg Arg Gly Leu Arg His
1               5

<210> SEQ ID NO 91
<211> LENGTH: 4
<212> TYPE: PRT
<213> ORGANISM: Artificial sequence
<220> FEATURE:
<223> OTHER INFORMATION: Example of sequence not allowable within the
      sequence motif

<400> SEQUENCE: 91

Lys Arg Lys Lys
1

<210> SEQ ID NO 92
<211> LENGTH: 4
<212> TYPE: PRT
<213> ORGANISM: Artificial sequence
<220> FEATURE:
<223> OTHER INFORMATION: Example of sequence not allowable within the
      sequence motif

<400> SEQUENCE: 92

Arg Arg Arg Arg
1

<210> SEQ ID NO 93
<211> LENGTH: 18
<212> TYPE: PRT
<213> ORGANISM: Unknown
<220> FEATURE:
<223> OTHER INFORMATION: SMAP-29 sheep;aa1-18

<400> SEQUENCE: 93

Arg Gly Leu Arg Arg Leu Gly Arg Lys Ile Ala His Gly Val Lys Lys
1               5                   10                  15

Tyr Gly

<210> SEQ ID NO 94
<211> LENGTH: 25
<212> TYPE: PRT
<213> ORGANISM: Artificial sequence
<220> FEATURE:
<223> OTHER INFORMATION: Mutated peptide deriving from Cecropin A (A.
      aegypti)

<400> SEQUENCE: 94
```

```
Gly Gly Leu Lys Lys Leu Gly Lys Leu Lys Lys Ala Gly Lys Arg
1               5                   10                  15

Val Phe Lys Ala Ala Lys Lys Ala Leu
            20                  25

<210> SEQ ID NO 95
<211> LENGTH: 28
<212> TYPE: PRT
<213> ORGANISM: Artificial sequence
<220> FEATURE:
<223> OTHER INFORMATION: Mutated peptide deriving from BMAP-28

<400> SEQUENCE: 95

Arg Gly Leu Arg Arg Leu Gly Arg Lys Ile Leu Arg Ala Trp Lys Lys
1               5                   10                  15

Tyr Gly Pro Ile Ile Val Pro Ile Ile Arg Ile Gly
            20                  25

<210> SEQ ID NO 96
<211> LENGTH: 17
<212> TYPE: PRT
<213> ORGANISM: Artificial Sequence
<220> FEATURE:
<223> OTHER INFORMATION: Mutated peptide deriving from MSI-78 (4-20)
      peptide

<400> SEQUENCE: 96

Arg Phe Leu Arg Arg Ala Arg Arg Phe Gly Arg Ala Phe Val Arg Ile
1               5                   10                  15

Leu

<210> SEQ ID NO 97
<211> LENGTH: 26
<212> TYPE: PRT
<213> ORGANISM: Artificial sequence
<220> FEATURE:
<223> OTHER INFORMATION: Mutated peptide deriving from magainin

<400> SEQUENCE: 97

Gly Ile Lys Lys Phe Leu Lys Ser Ala Lys Lys Phe Gly Lys Ala Phe
1               5                   10                  15

Lys Lys Val Ile Arg Gly Gly Gly Gly Ser
            20                  25

<210> SEQ ID NO 98
<211> LENGTH: 20
<212> TYPE: PRT
<213> ORGANISM: Artificial sequence
<220> FEATURE:
<223> OTHER INFORMATION: Mutated peptide deriving from HPA-NT3 peptide

<400> SEQUENCE: 98

Lys Arg Leu Lys Lys Leu Ala Lys Lys Ile Trp Lys Trp Gly Arg Arg
1               5                   10                  15

Gly Pro Gly Ser
            20

<210> SEQ ID NO 99
<211> LENGTH: 29
<212> TYPE: PRT
<213> ORGANISM: Artificial sequence
<220> FEATURE:
<223> OTHER INFORMATION: Mutated peptide deriving from amino acids
      298-326 of the alpha subunit of stonustoxin
```

<400> SEQUENCE: 99

Ile Lys Leu Ile Lys Arg Val Ile Lys Lys Phe Lys Lys Ile Phe Arg
1               5                   10                  15

Lys Tyr Pro Leu Thr Val Lys Lys Gly Ile Ala Val Gly
            20                  25

<210> SEQ ID NO 100
<211> LENGTH: 27
<212> TYPE: PRT
<213> ORGANISM: Artificial sequence
<220> FEATURE:
<223> OTHER INFORMATION: Mutated peptide deriving from amino acids 26-48
      of CagL protein

<400> SEQUENCE: 100

Gly Leu Lys Lys Leu Lys Arg Val Tyr Arg Lys Trp Val Lys Ala Val
1               5                   10                  15

Lys Lys Val Leu Lys Leu Gly Gly Gly Gly Ser
            20                  25

<210> SEQ ID NO 101
<211> LENGTH: 22
<212> TYPE: PRT
<213> ORGANISM: Artificial sequence
<220> FEATURE:
<223> OTHER INFORMATION: Mutated peptide deriving from amino acids 26-48
      of CagL protein

<400> SEQUENCE: 101

Gly Leu Lys Val Leu Lys Lys Ala Tyr Arg Arg Ile Arg Lys Ala Val
1               5                   10                  15

Arg Lys Ile Leu Lys Ala
            20

<210> SEQ ID NO 102
<211> LENGTH: 19
<212> TYPE: PRT
<213> ORGANISM: Artificial sequence
<220> FEATURE:
<223> OTHER INFORMATION: Mutated peptide deriving from amino acids
      178-196 of IE1 protein

<400> SEQUENCE: 102

Tyr Lys Arg Ala Phe Lys Lys Val Leu Lys Arg Ile Arg Arg Tyr Ala
1               5                   10                  15

Lys Arg Ser

<210> SEQ ID NO 103
<211> LENGTH: 24
<212> TYPE: PRT
<213> ORGANISM: Artificial sequence
<220> FEATURE:
<223> OTHER INFORMATION: synthetic sequence

<400> SEQUENCE: 103

Gly Phe Phe Lys Lys Ala Trp Arg Lys Val Lys His Ala Gly Arg Arg
1               5                   10                  15

Val Leu Lys Thr Ala Lys Gly Val
            20

<210> SEQ ID NO 104
<211> LENGTH: 20
<212> TYPE: PRT

<213> ORGANISM: unknown
<220> FEATURE:
<223> OTHER INFORMATION: CAP18AA

<400> SEQUENCE: 104

Gly Leu Arg Lys Ala Leu Arg Lys Phe Arg Asn Lys Ile Lys Glu Ala
1               5                   10                  15

Leu Lys Lys Ile
            20

<210> SEQ ID NO 105
<211> LENGTH: 20
<212> TYPE: PRT
<213> ORGANISM: artificial sequence
<220> FEATURE:
<223> OTHER INFORMATION: synthetic sequence

<400> SEQUENCE: 105

Gly Leu Arg Lys Ala Leu Arg Lys Phe Arg Lys Lys Ile Lys Glu Ala
1               5                   10                  15

Leu Lys Lys Ile
            20

<210> SEQ ID NO 106
<211> LENGTH: 29
<212> TYPE: PRT
<213> ORGANISM: artificial sequence
<220> FEATURE:
<223> OTHER INFORMATION: synthetic sequence

<400> SEQUENCE: 106

Arg Gly Leu Arg Arg Leu Gly Arg Lys Ile Ala Arg Gly Val Lys Lys
1               5                   10                  15

Tyr Gly Pro Thr Val Leu Arg Ile Ile Arg Ile Ala Gly
            20                  25

<210> SEQ ID NO 107
<211> LENGTH: 29
<212> TYPE: PRT
<213> ORGANISM: Artificial sequence
<220> FEATURE:
<223> OTHER INFORMATION: synthetic sequence

<400> SEQUENCE: 107

Arg Gly Leu Arg Arg Leu Gly Arg Lys Ile Ala His Gly Val Lys Lys
1               5                   10                  15

Tyr Gly Pro Thr Val Leu Arg His His His His His His
            20                  25

<210> SEQ ID NO 108
<211> LENGTH: 29
<212> TYPE: PRT
<213> ORGANISM: Artificial sequence
<220> FEATURE:
<223> OTHER INFORMATION: synthetic sequence

<400> SEQUENCE: 108

Arg Gly Ile Arg Lys Val Leu Lys Phe Ala Lys Arg Leu Phe Arg Lys
1               5                   10                  15

Ile Gly Arg Lys Pro Lys Gly Leu Ile Arg Val Gly Ala
            20                  25

<210> SEQ ID NO 109
<211> LENGTH: 25

```
<212> TYPE: PRT
<213> ORGANISM: Artificial sequence
<220> FEATURE:
<223> OTHER INFORMATION: synthetic sequence

<400> SEQUENCE: 109

Gly Arg Leu Phe Lys Arg Leu Ala Lys Lys Val Ala Lys Thr Val Arg
1               5                   10                  15

Lys Phe Gly Arg Lys Ile Gly Ala Leu
            20                  25

<210> SEQ ID NO 110
<211> LENGTH: 29
<212> TYPE: PRT
<213> ORGANISM: Pantholops hodgsoni

<400> SEQUENCE: 110

Arg Gly Leu Arg Arg Leu Gly Arg Lys Ile Leu His Gly Leu Lys Thr
1               5                   10                  15

Tyr Gly Pro Ile Val Ile Pro Leu Ile Arg Leu Gly Gly
            20                  25

<210> SEQ ID NO 111
<211> LENGTH: 4
<212> TYPE: PRT
<213> ORGANISM: artificial
<220> FEATURE:
<223> OTHER INFORMATION: linker

<400> SEQUENCE: 111

Gly Ala Gly Ala
1

<210> SEQ ID NO 112
<211> LENGTH: 8
<212> TYPE: PRT
<213> ORGANISM: artificial
<220> FEATURE:
<223> OTHER INFORMATION: linker

<400> SEQUENCE: 112

Gly Ala Gly Ala Gly Ala Gly Ala
1               5

<210> SEQ ID NO 113
<211> LENGTH: 12
<212> TYPE: PRT
<213> ORGANISM: artificial
<220> FEATURE:
<223> OTHER INFORMATION: linker

<400> SEQUENCE: 113

Gly Ala Gly Ala Gly Ala Gly Ala Gly Ala Gly Ala
1               5                   10

<210> SEQ ID NO 114
<211> LENGTH: 195
<212> TYPE: PRT
<213> ORGANISM: Artificial sequence
<220> FEATURE:
<223> OTHER INFORMATION: Fusion of SMAP-29 peptide and the endolysin of
      Citrobacter koseri phage CkP1, with the additional technical
      modification of a C54S mutation

<400> SEQUENCE: 114

Ala Arg Gly Leu Arg Arg Leu Gly Arg Lys Ile Ala His Gly Val Lys
```

```
1               5                  10                 15
Lys Tyr Gly Pro Thr Val Leu Arg Ile Ile Arg Ile Ala Gly Gly Ser
                20                  25                 30

Asn Ile Phe Lys Met Leu Arg Ile Asp Glu Gly Tyr Asp Ser Lys Ile
                35                  40                 45

Tyr Lys Asp Thr Glu Gly Phe Trp Thr Ile Gly Ile Gly His Leu Leu
            50                  55                 60

Thr Arg Asp Pro Ser Leu Glu Val Ala Lys Arg Glu Leu Asp Lys Leu
65                  70                  75                 80

Val Gly Arg Lys Ser Asn Gly Gln Ile Thr Gln Ser Glu Ala Glu Lys
                    85                  90                 95

Ile Phe Ala Asp Asp Val Asp Lys Ala Ile Asn Gly Ile Lys Lys Asn
                100                 105                110

Ala Ser Leu Lys Pro Val Tyr Asp Ser Leu Asp Gly Asp Asp Pro Arg
                115                 120                125

Gln Ala Ala Leu Ile Asn Met Val Phe Gln Met Gly Val Ala Gly Val
            130                 135                 140

Ala Gly Phe Thr Asn Ser Met Arg Met Val Lys Glu Lys Arg Trp Ala
145                 150                 155                160

Asp Ala Ala Val Asn Leu Ala Gln Ser Lys Trp Tyr Arg Gln Thr Pro
                    165                 170                175

Asn Arg Ala Lys Arg Val Ile Glu Thr Phe Arg Thr Gly Thr Trp Asn
                180                 185                 190

Ala Tyr Lys
        195

<210> SEQ ID NO 115
<211> LENGTH: 195
<212> TYPE: PRT
<213> ORGANISM: Artificial sequence
<220> FEATURE:
<223> OTHER INFORMATION: Fusion of a peptide comprising the preferred
      sequence motif for the peptide component and the endolysin of
      Enterobacteria phage CC31, with the additional technical
      modification of a C54S mutation

<400> SEQUENCE: 115

Ala Arg Gly Leu Arg Arg Leu Gly Arg Lys Ile Ala Arg Gly Val Lys
1               5                  10                 15

Lys Tyr Gly Pro Thr Val Leu Arg Ile Ile Arg Ile Ala Gly Gly Ser
                20                  25                 30

Asp Ile Phe Gly Met Leu Arg Ile Asp Glu Gly Tyr Asp Ser Lys Ile
                35                  40                 45

Tyr Lys Asp Thr Glu Gly Phe Trp Thr Ile Gly Ile Gly His Leu Leu
            50                  55                 60

Thr Arg Asp Pro Ser Leu Asp Val Ala Lys Arg Glu Leu Asp Lys Leu
65                  70                  75                 80

Val Gly Arg Pro Ser Asn Gly Gln Ile Thr Lys Ala Glu Ala Glu Ala
                    85                  90                 95

Ile Phe Ala Lys Asp Val Asp Lys Ala Thr Arg Gly Ile Leu Gly Asn
                100                 105                110

Ala Val Leu Lys Pro Val Tyr Asp Val Leu Asp Gly Val Arg Arg Ala
                115                 120                125

Ala Leu Ile Asn Met Val Phe Gln Met Gly Val Ala Gly Val Ala Ser
            130                 135                 140

Phe Pro Ala Ser Met Arg Leu Leu Lys Ser Lys Gln Trp Glu Ala Ala
```

```
                145                 150                 155                 160
Ala Lys Glu Leu Ala Asn Ser Lys Trp Tyr Arg Gln Thr Pro Asn Arg
                    165                 170                 175

Ala Lys Arg Val Ile Ala Thr Phe Lys Thr Gly Thr Trp Lys Ala Tyr
                    180                 185                 190

Glu Asn Leu
        195
```

<210> SEQ ID NO 116
<211> LENGTH: 195
<212> TYPE: PRT
<213> ORGANISM: Artificial sequence
<220> FEATURE:
<223> OTHER INFORMATION: Fusion of a peptide comprising the preferred
      sequence motif for the peptide component and the endolysin of
      Citrobacter koseri phage CkP1, with the additional technical
      modification of a C54S mutation

<400> SEQUENCE: 116

```
Met Arg Gly Leu Arg Arg Leu Gly Arg Lys Ile Ala His Gly Val Lys
1               5                   10                  15

Lys Tyr Gly Pro Thr Val Leu Arg His His His His His His Gly Ser
                20                  25                  30

Asn Ile Phe Lys Met Leu Arg Ile Asp Glu Gly Tyr Asp Ser Lys Ile
                35                  40                  45

Tyr Lys Asp Thr Glu Gly Phe Trp Thr Ile Gly Ile Gly His Leu Leu
            50                  55                  60

Thr Arg Asp Pro Ser Leu Glu Val Ala Lys Arg Glu Leu Asp Lys Leu
65                  70                  75                  80

Val Gly Arg Lys Ser Asn Gly Gln Ile Thr Gln Ser Glu Ala Glu Lys
                85                  90                  95

Ile Phe Ala Asp Asp Val Asp Lys Ala Ile Asn Gly Ile Lys Lys Asn
                100                 105                 110

Ala Ser Leu Lys Pro Val Tyr Asp Ser Leu Asp Gly Asp Pro Arg
                115                 120                 125

Gln Ala Ala Leu Ile Asn Met Val Phe Gln Met Gly Val Ala Gly Val
            130                 135                 140

Ala Gly Phe Thr Asn Ser Met Arg Met Val Lys Glu Lys Arg Trp Ala
145                 150                 155                 160

Asp Ala Ala Val Asn Leu Ala Gln Ser Lys Trp Tyr Arg Gln Thr Pro
                    165                 170                 175

Asn Arg Ala Lys Arg Val Ile Glu Thr Phe Arg Thr Gly Thr Trp Asn
                180                 185                 190

Ala Tyr Lys
        195
```

<210> SEQ ID NO 117
<211> LENGTH: 195
<212> TYPE: PRT
<213> ORGANISM: Artificial sequence
<220> FEATURE:
<223> OTHER INFORMATION: Fusion of a peptide comprising the preferred
      sequence motif for the peptide component and the endolysin of
      Enterobacteria phage CC31, with the additional technical
      modification of a C54S mutation

<400> SEQUENCE: 117

```
Ala Arg Gly Ile Arg Lys Val Leu Lys Phe Ala Lys Arg Leu Phe Arg
1               5                   10                  15
```

```
Lys Ile Gly Arg Lys Pro Lys Gly Leu Ile Arg Val Gly Ala Gly Ser
            20                  25                  30

Asp Ile Phe Gly Met Leu Arg Ile Asp Glu Gly Tyr Asp Ser Lys Ile
        35                  40                  45

Tyr Lys Asp Thr Glu Gly Phe Trp Thr Ile Gly Ile Gly His Leu Leu
    50                  55                  60

Thr Arg Asp Pro Ser Leu Asp Val Ala Lys Arg Glu Leu Asp Lys Leu
65                  70                  75                  80

Val Gly Arg Pro Ser Asn Gly Gln Ile Thr Lys Ala Glu Ala Glu Ala
                85                  90                  95

Ile Phe Ala Lys Asp Val Asp Lys Ala Thr Arg Gly Ile Leu Gly Asn
            100                 105                 110

Ala Val Leu Lys Pro Val Tyr Asp Val Leu Asp Gly Val Arg Arg Ala
        115                 120                 125

Ala Leu Ile Asn Met Val Phe Gln Met Gly Val Ala Gly Val Ala Ser
130                 135                 140

Phe Pro Ala Ser Met Arg Leu Leu Lys Ser Lys Gln Trp Glu Ala Ala
145                 150                 155                 160

Ala Lys Glu Leu Ala Asn Ser Lys Trp Tyr Arg Gln Thr Pro Asn Arg
            165                 170                 175

Ala Lys Arg Val Ile Ala Thr Phe Lys Thr Gly Thr Trp Lys Ala Tyr
        180                 185                 190

Glu Asn Leu
        195

<210> SEQ ID NO 118
<211> LENGTH: 192
<212> TYPE: PRT
<213> ORGANISM: Artificial Sequence
<220> FEATURE:
<223> OTHER INFORMATION: Fusion of a peptide comprising the preferred
      sequence motif for the peptide component and the endolysin of
      Serratia phage CHI14, with the additional technical modification
      of a C54S mutation

<400> SEQUENCE: 118

Ala Arg Gly Leu Arg Arg Leu Gly Arg Lys Ile Ala Arg Gly Val Lys
1               5                   10                  15

Lys Tyr Gly Pro Thr Val Leu Arg Ile Ile Arg Ile Ala Gly Gly Ser
            20                  25                  30

Asp Ile Phe Gly Met Leu Arg Ile Asp Glu Gly Tyr Asp Ser Lys Ile
        35                  40                  45

Tyr Lys Asp Thr Glu Gly Tyr Trp Thr Ile Gly Ile Gly His Leu Leu
    50                  55                  60

Thr Lys Asn Pro Ser Leu Ser Val Ala Lys Ala Glu Leu Asp Lys Leu
65                  70                  75                  80

Val Gly Arg Ser Ser Asn Gly Gln Ile Thr Gln Asp Glu Ala Glu Ser
                85                  90                  95

Ile Phe Ala Lys Asp Val Glu Lys Val Lys Gly Ile Gln Gly Asn
            100                 105                 110

Ser Val Leu Lys Pro Val Tyr Asp Ser Leu Asp Glu Ile Arg Arg Ala
        115                 120                 125

Ala Leu Ile Asn Met Val Phe Gln Met Gly Val Ala Gly Val Ala Gly
130                 135                 140

Phe Thr Asn Ser Met Arg Met Leu Lys Glu Lys Arg Trp Asp Glu Ala
145                 150                 155                 160
```

```
Ala Val Asn Leu Ala Lys Ser Arg Trp Tyr Asn Gln Thr Thr Asn Arg
            165                 170                 175

Ala Lys Arg Val Ile Ser Thr Phe Lys Thr Gly Thr Trp Gly Ala Tyr
        180                 185                 190
```

<210> SEQ ID NO 119
<211> LENGTH: 193
<212> TYPE: PRT
<213> ORGANISM: Artificial sequence
<220> FEATURE:
<223> OTHER INFORMATION: Fusion of a peptide according to SEQ ID NO 107
    and the endolysin of Serratia phage CHI14, with the additional
    technical modification of a C54S mutation

<400> SEQUENCE: 119

```
Ala Lys Phe Phe Arg Lys Leu Lys Lys Ser Val Lys Lys Arg Ala Lys
1               5                   10                  15

Arg Phe Phe Lys Lys Pro Arg Val Ile Gly Val Ser Ile Pro Phe Gly
            20                  25                  30

Ser Asp Ile Phe Gly Met Leu Arg Ile Asp Glu Gly Tyr Asp Ser Lys
        35                  40                  45

Ile Tyr Lys Asp Thr Glu Gly Tyr Trp Thr Ile Gly Ile Gly His Leu
50                  55                  60

Leu Thr Lys Asn Pro Ser Leu Ser Val Ala Lys Ala Glu Leu Asp Lys
65                  70                  75                  80

Leu Val Gly Arg Ser Ser Asn Gly Gln Ile Thr Gln Asp Glu Ala Glu
                85                  90                  95

Ser Ile Phe Ala Lys Asp Val Glu Lys Ala Val Lys Gly Ile Gln Gly
            100                 105                 110

Asn Ser Val Leu Lys Pro Val Tyr Asp Ser Leu Asp Glu Ile Arg Arg
        115                 120                 125

Ala Ala Leu Ile Asn Met Val Phe Gln Met Gly Val Ala Gly Val Ala
130                 135                 140

Gly Phe Thr Asn Ser Met Arg Met Leu Lys Glu Lys Arg Trp Asp Glu
145                 150                 155                 160

Ala Ala Val Asn Leu Ala Lys Ser Arg Trp Tyr Asn Gln Thr Thr Asn
                165                 170                 175

Arg Ala Lys Arg Val Ile Ser Thr Phe Lys Thr Gly Thr Trp Gly Ala
            180                 185                 190

Tyr
```

<210> SEQ ID NO 120
<211> LENGTH: 190
<212> TYPE: PRT
<213> ORGANISM: Artificial sequence
<220> FEATURE:
<223> OTHER INFORMATION: Fusion of a peptide comprising the preferred
    sequence motif for the peptide component and the endolysin of
    Citrobacter koseri phage CkP1, with the additional technical
    modification of a C54S mutation

<400> SEQUENCE: 120

```
Gly Arg Leu Phe Lys Arg Leu Ala Lys Lys Val Ala Lys Thr Val Arg
1               5                   10                  15

Lys Phe Gly Arg Lys Ile Gly Ala Leu Gly Ser Asn Ile Phe Lys Met
            20                  25                  30

Leu Arg Ile Asp Glu Gly Tyr Asp Ser Lys Ile Tyr Lys Asp Thr Glu
        35                  40                  45

Gly Phe Trp Thr Ile Gly Ile Gly His Leu Leu Thr Arg Asp Pro Ser
```

```
Leu Glu Val Ala Lys Arg Glu Leu Asp Lys Leu Val Gly Arg Lys Ser
 65                  70                  75                  80

Asn Gly Gln Ile Thr Gln Ser Glu Ala Glu Lys Ile Phe Ala Asp Asp
                 85                  90                  95

Val Asp Lys Ala Ile Asn Gly Ile Lys Lys Asn Ala Ser Leu Lys Pro
            100                 105                 110

Val Tyr Asp Ser Leu Asp Gly Asp Pro Arg Gln Ala Ala Leu Ile
            115                 120                 125

Asn Met Val Phe Gln Met Gly Val Ala Gly Val Ala Gly Phe Thr Asn
            130                 135                 140

Ser Met Arg Met Val Lys Glu Lys Arg Trp Ala Asp Ala Ala Val Asn
145                 150                 155                 160

Leu Ala Gln Ser Lys Trp Tyr Arg Gln Thr Pro Asn Arg Ala Lys Arg
                165                 170                 175

Val Ile Glu Thr Phe Arg Thr Gly Thr Trp Asn Ala Tyr Lys
            180                 185                 190

<210> SEQ ID NO 121
<211> LENGTH: 195
<212> TYPE: PRT
<213> ORGANISM: Artificial sequence
<220> FEATURE:
<223> OTHER INFORMATION: Fusion of a peptide comprising the preferred
      sequence motif for the peptide component and the endolysin of
      Citrobacter koseri phage CkP1, with the additional technical
      modification of a C54S mutation

<400> SEQUENCE: 121

Ala Arg Gly Leu Arg Arg Leu Gly Arg Lys Ile Leu His Gly Leu Lys
 1               5                  10                  15

Thr Tyr Gly Pro Ile Val Ile Pro Leu Ile Arg Leu Gly Gly Gly Ser
             20                  25                  30

Asn Ile Phe Lys Met Leu Arg Ile Asp Glu Gly Tyr Asp Ser Lys Ile
             35                  40                  45

Tyr Lys Asp Thr Glu Gly Phe Trp Thr Ile Gly Ile Gly His Leu Leu
 50                  55                  60

Thr Arg Asp Pro Ser Leu Glu Val Ala Lys Arg Glu Leu Asp Lys Leu
 65                  70                  75                  80

Val Gly Arg Lys Ser Asn Gly Gln Ile Thr Gln Ser Glu Ala Glu Lys
                 85                  90                  95

Ile Phe Ala Asp Asp Val Asp Lys Ala Ile Asn Gly Ile Lys Lys Asn
            100                 105                 110

Ala Ser Leu Lys Pro Val Tyr Asp Ser Leu Asp Gly Asp Pro Arg
            115                 120                 125

Gln Ala Ala Leu Ile Asn Met Val Phe Gln Met Gly Val Ala Gly Val
            130                 135                 140

Ala Gly Phe Thr Asn Ser Met Arg Met Val Lys Glu Lys Arg Trp Ala
145                 150                 155                 160

Asp Ala Ala Val Asn Leu Ala Gln Ser Lys Trp Tyr Arg Gln Thr Pro
                165                 170                 175

Asn Arg Ala Lys Arg Val Ile Glu Thr Phe Arg Thr Gly Thr Trp Asn
            180                 185                 190

Ala Tyr Lys
        195
```

-continued

```
<210> SEQ ID NO 122
<211> LENGTH: 6
<212> TYPE: PRT
<213> ORGANISM: artificial sequence
<220> FEATURE:
<223> OTHER INFORMATION: His-Tag (6x)

<400> SEQUENCE: 122

His His His His His His
1               5

<210> SEQ ID NO 123
<211> LENGTH: 196
<212> TYPE: PRT
<213> ORGANISM: Artificial sequence
<220> FEATURE:
<223> OTHER INFORMATION: A fusion of Cecropin A. (A aegyptii) peptide
      with endolysin of Vibrio phage VvAW1(YP_007518361.1)

<400> SEQUENCE: 123

Met Gly Gly Leu Lys Lys Leu Gly Lys Lys Leu Glu Gly Ala Gly Lys
1               5                   10                  15

Arg Val Phe Asn Ala Ala Glu Lys Ala Leu Pro Val Val Ala Gly Ala
                20                  25                  30

Lys Ala Leu Arg Lys Gly Gly Ser Gly Gly Gly Ser Gly Ser Met
            35                  40                  45

Gly Phe Lys Phe Ser Glu Arg Ser Lys Ser Arg Met Ala Gly Val His
    50                  55                  60

Pro Glu Leu Val Leu Val Phe His Glu Ala Leu Ala Val Ser Pro Ile
65                  70                  75                  80

Asp Phe Gly Ile Pro Glu His Gly Gly Leu Arg Ser Ala Glu Glu Gln
                85                  90                  95

Tyr Ser Leu Phe Leu Asp Asn Lys Ser Lys Ala Asp Gly Tyr Asn Lys
            100                 105                 110

Leu Ser Asn His Gln Ser Gly Asn Ala Leu Asp Phe Tyr Ala Tyr Leu
        115                 120                 125

Asn Gly Ala Ala Ser Trp Asp Lys Val His Leu Ala Met Val Ala Ala
    130                 135                 140

Thr Ile Leu Ser Thr Ala Ala Arg Leu Lys Glu Gln Gly Lys Ile Ser
145                 150                 155                 160

Ile Ser Ile Arg Trp Gly Gly Thr Phe Gly Asn Lys Gly Arg Ser Phe
                165                 170                 175

His Gly Trp Asp Tyr Pro His Met Glu Val Ile Ser Leu Glu His His
            180                 185                 190

His His His His
        195

<210> SEQ ID NO 124
<211> LENGTH: 295
<212> TYPE: PRT
<213> ORGANISM: Artificial sequence
<220> FEATURE:
<223> OTHER INFORMATION: A fusion of Cecropin A. (A aegyptii) peptide
      with a mutated cell wall binding domain of the modular KZ144
      endolysin and Lys68 endolysin

<400> SEQUENCE: 124

Met Gly Gly Leu Lys Lys Leu Gly Lys Lys Leu Glu Gly Ala Gly Lys
1               5                   10                  15

Arg Val Phe Asn Ala Ala Glu Lys Ala Leu Pro Val Val Ala Gly Ala
                20                  25                  30
```

Lys Ala Leu Arg Lys Gly Ala Gly Ala Gly Ala Gly Ser Lys
                35                  40                  45

Val Leu Arg Lys Gly Asp Arg Gly Asp Glu Val Ser Gln Leu Gln Thr
 50                  55                  60

Leu Leu Asn Leu Ser Gly Tyr Asp Val Gly Lys Pro Asp Gly Ile Phe
 65                  70                  75                  80

Gly Asn Asn Thr Phe Asn Gln Val Val Lys Phe Gln Lys Asp Asn Ser
                85                  90                  95

Leu Asp Ser Asp Gly Ile Val Gly Lys Asn Thr Trp Ala Glu Leu Phe
                100                 105                 110

Ser Lys Tyr Ser Pro Pro Ile Pro Tyr Lys Thr Ile Pro Met Ser Asn
                115                 120                 125

Arg Asn Ile Ser Asp Asn Gly Ile Lys Phe Thr Ala Ala Phe Glu Gly
        130                 135                 140

Phe Arg Gly Thr Ala Tyr Arg Ala Thr Lys Asn Glu Lys Tyr Leu Thr
145                 150                 155                 160

Ile Gly Tyr Gly His Tyr Gly Ala Asp Val Lys Glu Gly Gln Lys Ile
                165                 170                 175

Thr Glu Gly Gln Gly Leu Leu Leu His Lys Asp Met Val Lys Ala
                180                 185                 190

Val Ala Ala Val Asp Ala Val Ala His Pro Pro Leu Asn Gln Ser Gln
        195                 200                 205

Phe Asp Ala Met Cys Asp Leu Val Tyr Asn Ala Gly Val Gly Val Ile
210                 215                 220

Ala Ala Ser Thr Gly Thr Gly Gln Ala Leu Arg Lys Gly Asp Val Ala
225                 230                 235                 240

Thr Leu Arg Asn Lys Leu Thr Gln Phe His Tyr Gln Asn Gly Lys Ser
                245                 250                 255

Leu Leu Gly Leu Arg Arg Arg Ala Ala Gly Arg Val Ala Leu Phe Asp
                260                 265                 270

Gly Met Leu Trp Gln Gln Ala Glu Ala Ile Gly Arg Gly Ala Lys Leu
                275                 280                 285

Glu His His His His His His
        290                 295

<210> SEQ ID NO 125
<211> LENGTH: 223
<212> TYPE: PRT
<213> ORGANISM: Artificial sequence
<220> FEATURE:
<223> OTHER INFORMATION: Fusion of a modified peptide (SEQ ID NO:110)
      and endolysin of Pseudomonas phage vB_PsyM_KIL1

<400> SEQUENCE: 125

Met Gly Leu Arg Lys Ala Leu Arg Lys Phe Arg Lys Lys Ile Lys Glu
1               5                   10                  15

Ala Leu Lys Lys Ile Gly Gly Gly Ser Gly Ser Met Leu Ser Glu
                20                  25                  30

Lys Ser Phe Val Glu Ala Ala Ser Leu Gly Cys Glu Val Ala Ala
                35                  40                  45

Ile Lys Ala Ile Ala Ser Val Glu Thr Lys Gly Ser Ala Trp Ile Thr
        50                  55                  60

Pro Gly Val Pro Gln Ile Leu Tyr Glu Arg His Ile Met Ala Arg Leu
65                  70                  75                  80

Leu Lys Ala Lys Gly Val Pro Ile Ala Gly Leu Pro Ser Asp Leu Val

-continued

```
                      85                      90                      95
Asn Thr Thr Pro Gly Gly Tyr Gly Lys Phe Ser Glu Gln His Gly Lys
                100                     105                     110

Leu Asp Arg Ala Val Lys Ile Asp Arg Glu Cys Ala Leu Gln Ser Cys
        115                     120                     125

Ser Trp Gly Met Phe Gln Leu Met Gly Phe Asn Tyr Lys Leu Cys Gly
    130                     135                     140

Tyr Ala Thr Val Gln Ala Phe Val Asn Ala Met Tyr Lys Ser Glu Asp
145                     150                     155                 160

Glu Gln Leu Asn Ala Phe Val Gly Phe Ile Lys Ser Asn Leu Gln Leu
                165                     170                     175

Asn Asp Ala Leu Lys Ser Lys Asp Trp Ala Thr Val Ala Arg Leu Tyr
                180                     185                     190

Asn Gly Ala Asp Tyr Lys Ile Asn Ser Tyr Asp Gln Lys Leu Ala Val
            195                     200                     205

Ala Tyr Glu Ser Asn Lys Arg Leu Glu His His His His His His
    210                     215                     220
```

The invention claimed is:

1. A polypeptide comprising a Gram negative endolysin and a peptide selected from the group consisting of an antimicrobial peptide, an amphipathic peptide, a cationic peptide, a sushi peptide and a defensin,
wherein the endolysin is selected from the group consisting of SEQ ID NO:7, SEQ ID NO:8, and SEQ ID NO:9.

2. The polypeptide according to claim 1, wherein the peptide is an antimicrobial peptide or an amphipathic peptide.

3. The polypeptide according to claim 1, wherein the peptide comprises a sequence motif which:
   i) is 16, 17, 18, 19 or 20 amino acids in length;
   ii) comprises at least 40% and at most 60% amino acids selected from a first group of amino acids consisting of lysine, arginine and histidine,
   wherein each amino acid of said at least 40% and at most 60% amino acids is selected independently from said first group,
   wherein each amino acid selected from this first group is arranged in said sequence motif either alone, pairwise together with a further amino acid selected from the first group, or in a row with 2 further amino acids selected from the first group, but does not occur in a row with 3 or more further amino acids selected from the first group, wherein at least 2 pairs of amino acids selected from the first group are present in said sequence motif, and wherein at most one row with 3 of the amino acids selected from the first group is present in said sequence motif, with the additional proviso, that if such row with 3 amino acids of the first group is present in said sequence motif, then the amino acids at positions −12, −11, −8, −5, −4, +6, +7, +10, +13, and +14 relative to the first amino acid of the 3 amino acids in a row are, provided the respective position exists in said sequence motif, not selected from said first group;
   iii) comprises at least 40% and at most 60% amino acids selected from a second group of amino acids consisting of alanine, glycine, isoleucine, leucine, phenylalanine, serine, threonine, tryptophan, tyrosine and valine;
   wherein each amino acid of said at least 40% and at most 60% amino acids selected from the second group is selected independently from said second group; and
   iv) wherein the remaining amino acids of said sequence motif, if any are present in the motif, are selected from a third group consisting of asparagine, aspartic acid, glutamine, glutamic acid, methionine, and cysteine, wherein each of said amino acids is selected independently from said third group.

4. The polypeptide according to claim 3, wherein the peptide comprises the sequence according to SEQ ID NO:37, SEQ ID NO:106, SEQ ID NO:107, SEQ ID NO:108, SEQ ID NO:109 or SEQ ID NO:110.

5. The polypeptide according to claim 3, wherein at least three different amino acids are selected from the second group, if the sum of amino acids selected from the first group and selected from the second group yields 100% of the amino acids of the sequence motif.

6. The polypeptide according to claim 1, wherein the polypeptide comprises the amino acid sequence of SEQ ID NO:114, SEQ ID NO:115, SEQ ID NO:116, SEQ ID NO:117, SEQ ID NO:118, SEQ ID NO:119, SEQ ID NO:120, or SEQ ID NO:121.

7. The polypeptide according to claim 6, wherein the polypeptide comprises the amino acid sequence of SEQ ID NO:114 or SEQ ID NO:115.

8. The polypeptide according to claim 1, wherein the polypeptide degrades peptidoglycan of at least one Gram-negative bacterial species.

9. The polypeptide according to claim 8, wherein the polypeptide degrades the peptidoglycan of at least one Gram-negative bacterial species in absence of other outer membrane permeabilizing substances.

10. The polypeptide according to claim 9, wherein the polypeptide degrades the peptidoglycan of E. coli bacteria and/or P. aeruginosa bacteria in absence of outer membrane permeabilizing substances.

11. The polypeptide according to claim 8, wherein the polypeptide exhibits in absence of outer membrane permeabilizing substances a minimal inhibitory concentration (MIC) of 20 µg/ml or less for *Escherichia coli* (*E. coli*) strain RKI 06-08410.

12. The polypeptide according to claim 8, wherein the polypeptide degrades the peptidoglycan of *Escherichia coli* (*E. coli*) bacteria and/or *Pseudomonas aeruginosa* (*P. aeruginosa*) bacteria.

13. A method for treating Gram negative bacterial infection in a subject in need thereof, wherein the method comprises administering to said subject the polypeptide of claim 1, and wherein the polypeptide is administered without addition of further outer membrane permeabilizing substances.

14. A method of disinfecting a surface comprising contacting said surface with the polypeptide of claim 1, wherein the polypeptide is administered without addition of further outer membrane permeabilizing substances.

\* \* \* \* \*